(12) United States Patent
Lee

(10) Patent No.: US 11,435,311 B2
(45) Date of Patent: Sep. 6, 2022

(54) METHODS OF MANUFACTURING BIOSENSOR NANOWELLS

(71) Applicant: MARA NANOTECH KOREA, INC., Daejeon (KR)

(72) Inventor: Heayeon Lee, Oakland Gardens, NY (US)

(73) Assignee: MARA NANOTECH KOREA, INC., Daejeon (KR)

( * ) Notice: Subject to any disclaimer, the term of this patent is extended or adjusted under 35 U.S.C. 154(b) by 0 days.

(21) Appl. No.: 16/982,909

(22) PCT Filed: Mar. 22, 2019

(86) PCT No.: PCT/US2019/023633
§ 371 (c)(1),
(2) Date: Sep. 21, 2020

(87) PCT Pub. No.: WO2019/183504
PCT Pub. Date: Sep. 26, 2019

(65) Prior Publication Data
US 2021/0003527 A1   Jan. 7, 2021

Related U.S. Application Data

(60) Provisional application No. 62/647,280, filed on Mar. 23, 2018.

(30) Foreign Application Priority Data

Mar. 23, 2018   (KR) .................. 10-2018-0033974

(51) Int. Cl.
*G01N 27/327* (2006.01)
*G01N 27/38* (2006.01)
(Continued)

(52) U.S. Cl.
CPC ..... *G01N 27/3278* (2013.01); *G01N 27/3277* (2013.01); *G01N 27/38* (2013.01); *G01N 33/5438* (2013.01); *G03F 7/70* (2013.01)

(58) Field of Classification Search
CPC .......... G01N 27/3278; G01N 27/3277; G01N 27/38; G01N 33/5438; G03F 7/70
See application file for complete search history.

(56) References Cited

U.S. PATENT DOCUMENTS 6,514,762 B1    2/2003  Wang
2006/0151327 A1  7/2006  Sonnenberg et al.

FOREIGN PATENT DOCUMENTS

JP      2005164387 A    6/2005
KR    1020140081208 A   7/2014
(Continued)

OTHER PUBLICATIONS

Suri, Savan, "Fabrication of Nanoelectrode Arrays for Dopamine Detection" (2016). Graduate Theses, Dissertations, and Problem Reports. 6746. https://researchrepository.wvu.edu/etd/6746. (Year: 2016).*

(Continued)

*Primary Examiner* — Robert J Eom
(74) *Attorney, Agent, or Firm* — Morgan, Lewis & Bockius LLP

(57) ABSTRACT

Improved methods of manufacturing highly sensitive and selective electrochemical biosensors are provided. The method may comprise washing the nanowell array electrodes of the biosensors with ferricyanide, preferably potassium ferricyanide. The method may also comprise washing the electrodes of the biosensors with methylene blue (i.e., methylthioninium chloride), either in addition to the ferricyanide and/or H2SO4 washing steps, or without the ferricyanide and/or $H_2SO_4$ washing steps.

7 Claims, 29 Drawing Sheets

(51) Int. Cl.
 G01N 33/543 (2006.01)
 G03F 7/20 (2006.01)

(56) References Cited

FOREIGN PATENT DOCUMENTS

| KR | 101656997 B1 | 9/2016 |
| KR | 101717044 B1 | 3/2017 |
| KR | 102101941 B1 | 5/2020 |

OTHER PUBLICATIONS

International Search Report and Written Opinion for International application No. PCT/US2019/023633, dated Jun. 10, 2019, ISA/US.
Lee. "Hypersensitive Electrochemical Biosensors Based on Nanowell Array Structures for Point of Care Technology ." Northeastern.edu, Northeastern University, Aug. 2016. Entire Document, especially Abstract, pages xix-xx, 13, 15-17, 24, 42-43, 57, 62, 130.
Foguel, et al. "Comparison of Gold CD-R Types as Electrochemical Device and as Platform for Biosensors." Journal of the Brazilian Chemical Society, Brazilian Chemical Society, Apr. 2016, www.scielo.br/scielo.php?script=sci_arttext&pid=S0 103-50532016000400650.
Tolley et al. "Electrolytic Cleaning and Conditioning of Gold Redox Probes in Flotation Circuits." Centers for Disease Control and Prevention, Centers for Disease Control and Prevention, May 11, 1994, www.cdc.gov/niosh/nioshtic-2/10005129.html.
Gutierrez et al. "Bioimprinting as a Tool for the Detection of Aflatoxin B 1 Using a Capacitive Biosensor." Biotechnology Reports (Amsterdam, Netherlands), Elsevier, May 25, 2016, www.ncbi.nlm.nih.gov/pmc/articles/PMC5042299/.
Fischer, et al. "Gold Cleaning Methods for Electrochemical Detection Applications." Technical University of Denmark, Dec. 3, 2008. https://www.researchgate.net/publication/225291703_Gold_cleaning_methods_for _electrochemical_detection_applications.
Seo et al. "Electrochemical Nanobiosensor on Si3N4 Nanowell Array Electrode." Electrochemical Nanobiosensor on Si3N4 Nanowell Array Electrode I 75375, OMICS International, Nov. 2, 2017, www.omicsonline.org/proceedings/electrochemical-nanobiosensor-on-si3n4-nanowell-array-electrode-75375.html.

* cited by examiner

FIG. 1A
FIG. 1B
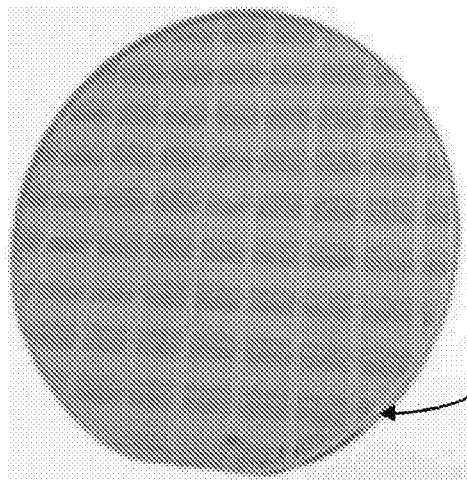
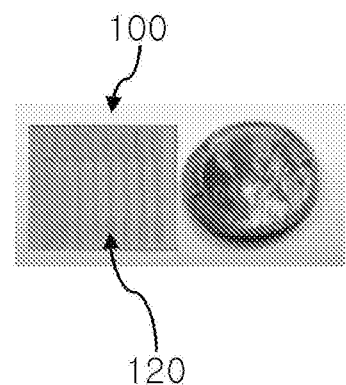
FIG. 1C
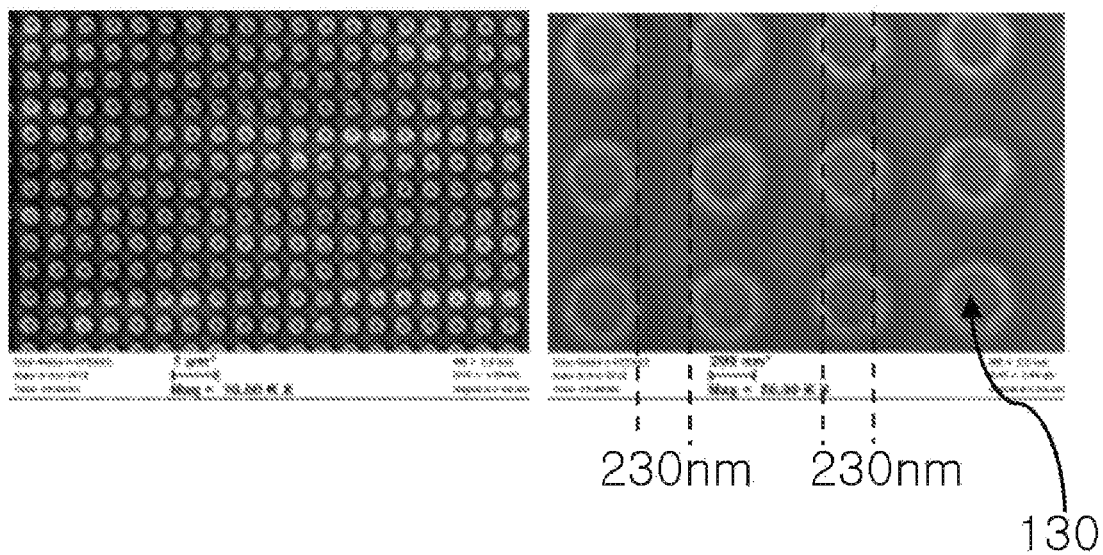

METHODS OF MANUFACTURING BIOSENSOR NANOWELLS

CROSS-REFERENCE TO RELATED APPLICATION

This application is a 371 U.S. national stage of PCT/US2019/023633, filed Mar. 22, 2019, which claims the benefit of priority from U.S. Provisional Application Ser. No. 62/647,280, filed Mar. 23, 2018 and Korean Patent Application No. 10-2018-0033974, filed Mar. 23, 2018, the contents of each of which are incorporated herein by reference.

FIELD OF THE INVENTION

The present disclosure is generally concerned with manufacturing methods for highly sensitive and selective biosensors. More particularly, the present disclosure concerns manufacturing methods for highly sensitive and selective biosensors that reduce or eliminate impurities from electrochemical biosensor.

BACKGROUND OF THE INVENTION

Biosensors are used to detect the presence of biological molecules such as proteins, amino acids (e.g., DNA and/or RNA containing specific base sequences), or other organic molecules. Some of the examples of biosensors include pregnancy tests and glucose monitoring sensors. These biosensors can detect biomolecules such as human chronic gonadotropin (hCG) or glucose that are present in bodily fluids such as blood or urine.

In order to detect specific analytes (e.g., biological molecules), biosensors may contain analyte-binding surface where probes specific for an analyte. (e.g., single-strand DNA or antibody specific for the target molecule) are immobilized to the analyte binding surface. Different types of biosensors using distinct scientific principles have been developed that can detect the presence of specific biological molecules.

Examples of different types of biosensors include electrochemical biosensors, nano-cantilever biosensors, and micro- or nano-electromechanical systems (MEMS/NEMS). Like other types of biosensors, electrochemical biosensors comprise an analyte-binding surface that is capable of interacting with and/or binding to specific biomolecules (e.g., a specific protein or a specific sequence of DNA). In particular, electrochemical biosensors use the principle of electrochemical analysis to detect specific analytes, where chemical response to an electrical excitation applied to a system is measured and analyzed to detect whether an analyte is bound to the surface of an electrode. Unlike nano-cantilever biosensors and MEMS/NEMS, electrochemical biosensors' signals can be directly detected by an electronic device for analysis, allowing for fast diagnosis.

Potential future applications for electrochemical biosensors include diagnosis in traditional medical and healthcare settings (e.g., blood and/or urine sample testing for specific biological molecules); medical diagnosis non-hospital settings (e.g., military use in combat zone and/or self-administered consumer diagnostics), non-medical detection of biological and/or small molecule detection (e.g., water quality testing, environmental testing, quality control and/or quality assurance testing in food industry); companion diagnostics for pharmaceutical therapeutics; research applications where detection of small molecules are required; and/or other settings or circumstances where detection of biological Molecules is needed. A person skilled in the art will appreciate that, although the present disclosure is called "biosensors," its application is not limited to detection of biological molecules. In other words, the present disclosure may be used for detection of other small non-biological (e.g., inorganic, metallic, solute, electrolyte, and/or elemental) molecules. In addition, although examples provided here consist of detection in fluidic and/or aqueous milieu, one skilled in the art will appreciate that the present disclosure may be used to detect small molecules in other fluidic milieu such as in oil, solvents, gas, and/or colloidal solutions.

In order for electrochemical biosensors to be adapted widely for a broad range of applications, the biosensors must be highly sensitive and selective, and cost of manufacturing of such sensor must be competitive. Electrochemical biosensors with significantly improved sensitivity and selectivity may enable miniaturization of such devices, which in turn may reduce the production cost and further contribute to adoption of electrochemical biosensors for a wide range of applications.

A particular type of highly sensitive and selective biosensors has been described in published US Patent Application No. US2017/0219554 A1, the content of which is herein incorporated by reference. These biosensors included a perforated insulation layer (or insulating layer) laid on an electrode of an electrochemical biosensor to form nanowells (or nano-wells). Such electrochemical biosensors can detect analytes that are present in fM-range in biological samples with high selectivity.

However, manufacturing of such biosensors is technically challenging. In particular, contamination of the biosensors with impurities during the manufacturing process can render the biosensor defective or adversely affect sensitivity and selectivity of the biosensor.

Accordingly, there is a need for improved methods of manufacturing highly sensitive and selective biosensors such those with perforated insulation layer laid on an electrode, where contamination of the biosensors with impurities is reduced or eliminated.

SUMMARY OF THE INVENTION

Improved methods of manufacturing highly sensitive and selective electrochemical biosensors are provided herein. One exemplary embodiment of the method comprises washing the nanowell (or nanowell) array electrodes of biosensors with ferricyanide, preferably potassium ferricyanide. In another exemplary embodiment, the method comprises washing the electrodes of the biosensors with $H_2SO_4$ and additionally washing the electrodes with ferricyanide. In another exemplary embodiment, the method comprises washing the electrodes of the biosensors with methylene blue (i.e., methylthioninium chloride), either in addition to the ferricyanide and/or $H_2SO_4$ washing steps, or without the ferricyanide and/or $H_2SO_4$ washing steps.

The methods disclosed herein result in removal of impurities from the biosensor. In some embodiments, the impurities are removed from the electrode (e.g., gold electrode) surface.

In one exemplary embodiment, the present invention is intended to improve production of electrochemical biosensor devices. One example of such a electrochemical biosensor device includes a plurality of electrodes made of a buffer layer laid on a substrate layer, an electrode layer laid on the buffer layer, and a perforated insulator layer laid on the electrode layer, such that a plurality of nanowells are formed on the electrode layer and the dimensions of the nanowells are defined by the sizes of the perforations, walls of the nanowells are defined by the insulator layer, and the bottom floors of the nanowells are defined by an upper surface of the electrode layer. In some instances, the nanowells of the biosensors have a pitch ratio of 1:1. In other instances, the biosensors can detect analytes that are present in fM concentration range.

In some embodiments, the electrochemical biosensor can include a glass substrate layer, silicon substrate layer, silicon dioxide insulator layer, titanium buffer layer, chromium buffer layer, and/or gold electrode layer.

In yet other embodiments, the electrochemical biosensor can have perforated insulator layer, wherein the perforations (e.g., bores and/or holes) may define dimensions of nanowells such that the nanowells are cylindrical in shape. In yet some other embodiments, the nanowells have circular openings with a diameter of about 230 nm, 100 nm, and/or 50 nm. In further yet other embodiments, the nanowells have pitch ratio of about 1:5, about 1:3 and/or about 1:1.

In some embodiments, the electrochemical biosensor can operate in conjunction with an electronic device, whereby the electrochemical biosensor is capable of sending signals to the electronic, device such that one or more electrochemical reaction parameters between the electrode containing a reference sample and the electrode containing a test sample can be detected by the electronic device using the signals to determine whether an analyte is present in the test sample. In an exemplary embodiment, the electrochemical reaction comprises oxidation reaction and reduction reaction. In a further exemplary embodiment, the parameters comprise variation in redox current.

In some other embodiments, the electrochemical biosensor can be used to detect analytes in sample solutions by (1) applying the test sample to sensing electrodes of the electrochemical biosensor to allow binding of any analytes that may be present in the test sample; (2) rinsing the sensing electrodes with an appropriate buffer to wash away any unbound and/or non-specifically bound analytes and/or non-analytes from the sensing electrodes; (3) applying electric current to the sensing electrode in such a way to cause chemical changes to the sensing electrode; (4) measuring electrochemical properties of the sensing electrode using an electronic device; and (5) analyzing a difference in electrochemical properties between the test sample and the reference sample to determine the presence of an analyte on the sensing electrode. In an exemplary embodiment, the electrochemical properties of the sensing electrode are measured using cyclic voltammetry analysis.

In another exemplary embodiment, the present invention provides a manufacturing method for biosensors comprising steps of forming a metal layer; forming an electrode layer by patterning the metal layer using a first photolithography process; forming an inorganic insulator layer on the electrode layer; forming a plurality of nanowells on the inorganic insulator layer wherein a part of the electrode layer is exposed by using a second photolithography process; and washing a plurality of nanowells to remove impurities from the exposed electrode layer by using $H_2SO_4$.

In some embodiments, the method further comprises washing nanowells by using a ferricyanide etching (or washing) after $H_2SO_4$ washing step. The ferricyanide etching washing step is performed immersing the biosensors in a mixed solution of $K_3Fe(CN)_6$ and KCl solution and applying the voltage of 1.0-1.5 V. For example, the ferricyanide etching may be performed at a temperature in the range of 15-25° C. for 1 to 10 seconds.

In some embodiments, the electrode comprises gold (Au), and the ferricyanide etching planarizes the surface of the electrode. The inorganic insulator layer comprises $SiO_2$ or $Si_3N_4$.

In some embodiments, $H_2SO_4$ washing step is performed immersing biosensors in $H_2SO_4$ solution and applying the voltage of 1.0-1.5 V for 1-5 minutes.

In some embodiments, the pitch ratio of the nanowells is defined as the size of each nanowell to the shortest distance between adjacent nano-wells, and may be 1:3 or less, preferably 1:1.

In another embodiments, the present invention provides a manufacturing method comprising steps of forming an electrode on a substrate layer; forming an inorganic insulator layer on the electrode; forming a plurality of nanowells on the insulator layer such that a part of the electrode is exposed using a photolithography process; a first washing step by immersing nanowells into $H_2SO_4$ solution and applying the voltage of 1.5-2.0 V; a secondary washing step by immersing nanowells into the mixed solution of $K_3Fe(CN)_6$ and KCl solution and applying the voltage of 1.0-1.5 V.

The present disclosure is also directed to methods of manufacturing highly sensitive and highly selective electrochemical biosensors that minimize contamination of the biosensor with impurities. In some embodiments, the washing step using a sulfuric acid solution after forming nanowells prevents adverse effects on the sensitivity and selectivity of biosensors, which are caused by contamination of biosensors, for example, contamination of electrodes on the surfaces of nanowells, with impurities during the manufacturing procedures. In some embodiments, in addition to the washing process using a sulfuric acid solution, a ferricyanide etching (or washing) process is used, thereby more efficiently removing contaminants, and improving the flatness of the electrode surface. Consequently, these processes improve the sensitivity and selectivity of biosensors.

The electrochemical biosensors manufactured according the manufacturing methods of the present invention can detect analytes that are present in fM concentration range in biological samples with a high specificity.

BRIEF DESCRIPTION OF THE DRAWINGS

FIGS. 1A-1D present photographic and microscopy images of an embodiment of present disclosure.

Figure 1D:
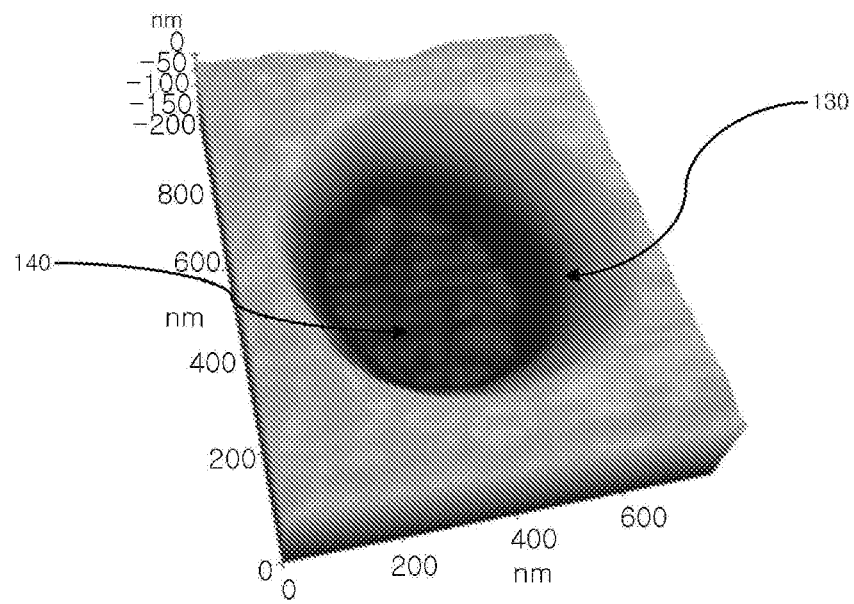

While the invention comprises embodiments in many different forms, there are shown in the drawings and will herein be described in detail several specific embodiments with the understanding that the present disclosure is to be considered as an exemplification of the principles of the technology and is not intended to limit the invention to the embodiments illustrated.

DETAILED DESCRIPTION OF THE INVENTION

Certain exemplary embodiments will now be described to provide an overall understanding of the principles of the method disclosed herein. One or more examples of these embodiments are illustrated in the accompanying drawings. Those skilled in the art will understand that the methods specifically described herein and illustrated in the accompanying drawings are non-limiting exemplary embodiments and that the scope of the present disclosure is defined solely by the claims. The features illustrated or described in collection with one exemplary embodiment may be combined with the features of other embodiments. Such modifications and variations are intended to be included within the scope of the present application.

Additionally, the figures are not necessarily to scale and, to the extent that linear or circular dimensions are used in the description of the disclosed devices and methods, such dimensions are not intended to limit the types of shapes and sizes that can be used in conjunction with such devices and methods. A person skilled in the art will recognize that an equivalent to such linear and circular dimensions can easily be determined for any geometric shape. Still further, sizes and shapes of the devices, and the components thereof, can depend at least on the anatomy of the subject in which the device will be used, the size and shape of components with which the device will be used, and the methods and procedures in which the device will be used.

Furthermore, while the exemplary embodiments provided herein describe method of production of devices capable of detecting biomolecules (e.g., proteins and/or nucleic acid molecules), a person skilled in the art will recognize that the device may be adopted to be used to detect presence of non-biological molecules and/or samples that are not biological samples. As an example, presence of inorganic material may be detected using biosensors made using the present invention for water quality testing, environmental testing and/or quality control/quality assurance testing in other industrial settings.

In order for an electrochemical sensor to be adopted in a wide range of applications such as diagnosis in traditional medical, pharmaceutical, and/or healthcare settings (e.g., blood and/or urine sample testing for specific biological molecules), Medical diagnosis in non-hospital settings (e.g., military use in combat zone, self-administered consumer diagnostics such as pregnancy test or blood glucose monitoring), non-medical detection of biological and/or small molecule detection (e.g., water quality testing, environmental testing, quality control and/or quality assurance testing in food industry), companion diagnostics for pharmaceutical therapeutics; research applications where detection of small molecules are required, and/or other settings or circumstances where detection of biological molecules is needed, the electrochemical sensor must be sensitive (i.e., being able to detect low concentrations of analyte), selective (i.e., being able to distinguish and differentiate target analytes in the presence of other components), easy to use (i.e., simple to operate, requires small amounts of test samples), and readily available to users (i.e., able to manufacture scalably, in large quantities, and/or at a low cost).

The present disclosure is directed to methods of manufacturing highly sensitive and highly selective electrochemical biosensors that minimize contamination of the biosensor with impurities.

Detailed Description of Electrochemical Biosensors

Various embodiments of the electrochemical biosensors are described. The methods of manufacturing described herein can be used to improve production of electrochemical biosensors such as those describe below and in published US Patent Application No. US2017/0219554 A1.

FIG. 1A-1D illustrate photographic and microscopy images of one embodiment of an electrochemical biosensor 100. As illustrated in FIG. 1A, a plurality of one embodiment of present disclosure 100 may be produced on a single substrate layer 110, such as a glass or silicon substrate layer (e.g., a wafer). FIG. 1B is a photographic image of a single electrochemical biosensor 100 comprising multiple sensing electrodes 120, FIG. 1C is a scanning electron microscopy image of the sensing electrode of FIG. 1B, comprising a plurality of nanowells 130 having a pitch ratio (ratio between the diameter of the nanowell openings and the shortest distance between neighboring nanowells) of approximately 1:1, and the nanowell opening diameter of approximately 230 nm. In other embodiments, the nanowell pitch ratio and/or the nanowell opening diameter may be of a different value, as disclosed in later portions of the present disclosure. FIG. 1D is a perspective atomic force microscopy image of a single nanowell 130, showing cylindrical dimensions of a nanowell 130 having a bottom floor 140 that is defined by the top surface of an electrode layer.

Figure 2:
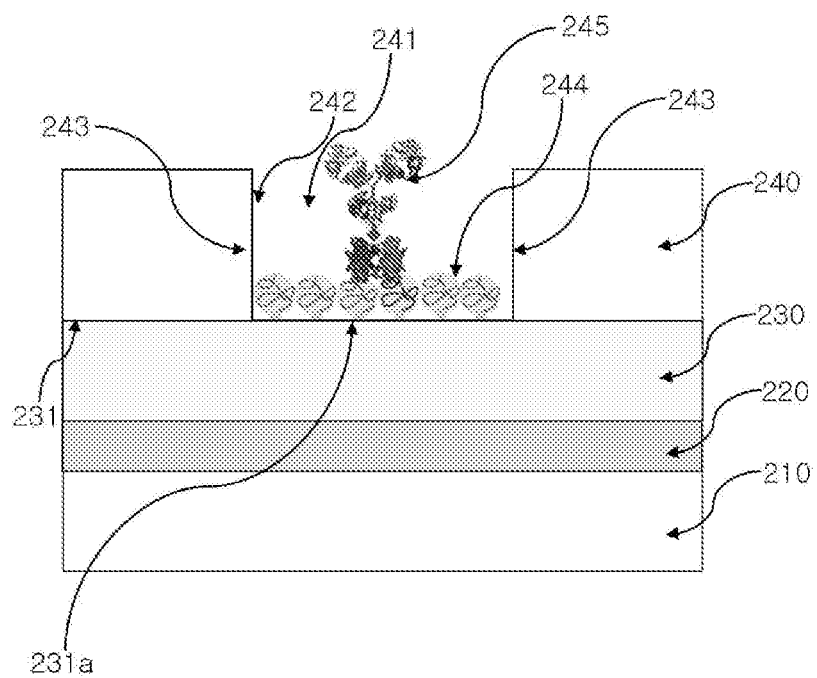
FIG. 2 presents a cross-sectional schematic diagram of an embodiment pf a sensing electrode.

FIG. 2 illustrates a sensing electrode of FIG. 1B which is a cross-sectional schematic representation of a nanowell portion of FIG. 1D. In one embodiment, the sensing electrode may comprise a glass or silicon substrate layer 210, a buffer layer 220, laid on the substrate layer, an electrode layer 230 laid on the substrate layer, and an insulator layer 240 laid on the electrode layer.

In one embodiment, the substrate layer 210 may be made of glass. The substrate layer may also comprise silicon, silicon dioxide (e.g., quartz), borosilicate, and/or other glass compositions used in semiconductor manufacturing. In other embodiments, the glass or silicon substrate layer 210 may be a circular wafer. In yet other embodiments, the glass or silicon substrate layer 210 may be configured to accommodate a plurality of electrochemical biosensors, as illustrated in FIG. 1A.

The buffer layer 220 of the sensing electrode 120 may provide enhanced bonding of the electrode layer 230 to the substrate layer 210 thereby minimizing risk of the electrode layer 230 detaching from the substrate layer 210. In other words, the buffer layer 220 allows the electrode layer 230 and the substrate layer 210 to form a tighter seal. Such enhanced bonding or formation of seal between the electrode layer 230 and substrate layer 210 may enable easier and more reliable manufacturing of the electrochemical biosensor and/or reduce cost of manufacture. In one preferred embodiment, the buffer layer may comprise titanium, chromium, and/or alloys of titanium or chromium.

The insulator layer 240 of the sensing electrode 120 may be perforated, such that the insulator layer 240 comprises a plurality of bores 241 (i.e., holes). The plurality of bores is also illustrated in FIG. 1C, the bores forming the nanowells 130. In a preferred embodiment, the bores 241 define the internal dimensions of a plurality of nanowells 242. In some embodiments, the bores 241 are cylindrical in shape, as shown in FIG. 1D, such that the nanowells 242 whose dimensions are defined by the bores 241 have a circular opening and the insulator layer form the walls 243 of the cylindrical nanowells 242. Because the perforated insulator layer 240 is laid on the electrode layer 230, by virtue of the relative positions between the two layers, the electrode layer's top surface 231 that is not covered by the insulator layer 240 may form the bottom surface of the nanowell 231a. In one preferred embodiment, the insulator layer 240 of the sensing electrode may comprise silicon nitride ($Si_3N_4$), because silicon nitride is more resilient and stable compared to certain alternatives, such as organic or inorganic polymers. In another preferred embodiment, the insulator layer 240 of the sensing electrode may comprise silicon dioxide ($SiO_2$). Features such as resilience and stability of silicon nitride may enable a more reliable and consistent manufacturing of the sensing electrode portion of the present disclosure, resulting in reduced occurrences of defective products and reduced cost of manufacture.

In some embodiments, where the opening of the nanowell is circular, the diameter of the circular opening of the nanowells 242 may be less than 1000 nm. In other embodiments, the diameter of the circular opening of the nanowells 242 may be less than 300 nm. In yet other embodiments, the diameter of the circular opening of the nanowells 242 may be approximately 230 nm, 100 am, and/or 50 am. Although the embodiments described above has nanowells 242 that are cylindrical in shape with a circular opening, a person skilled in the art will recognize that the nanowells 242 may have various other opening shapes, such as rectangular, oval, and/or polygonal shapes. In these embodiments having nanowells 242 with various other opening shapes, the dimension of the opening may be less than 1000 am or 300 am, or may be approximately 230 am, 100 am, and/or 50 am. In addition, a person skilled in the art will also recognize that the present invention is not limited to the compositions and structure described above, but may also include compositions and structure with similar characteristics, or improved characteristics.

In other embodiments, the bottom surfaces 231a of the nanowells 242 (e.g., top surface of the electrode layer that is not covered by the insulator layer) may comprise probe molecules 245 that are capable of binding with specific analytes. As an example, as shown in FIG. 2, biotinylated antibodies 245 specific for an analyte may be immobilized to the bottom surfaces 231a of the nanowells by using an intermediary binding molecule 244 such as avidin or streptavidin. A person skilled in the art will appreciate that other well-known methods of immobilizing analytes probes 245 can be incorporated into present disclosure, and are within the scope of present invention, as discussed below. In yet another preferred embodiment, the insulator layer 240 with a plurality of bores 241 may restrict binding of an analyte to its probes 245 to the bottom surfaces 231a of the nanowells 242, while preventing binding and/or aggregation of the analyte to the insulator layer 240.

Figure 3:
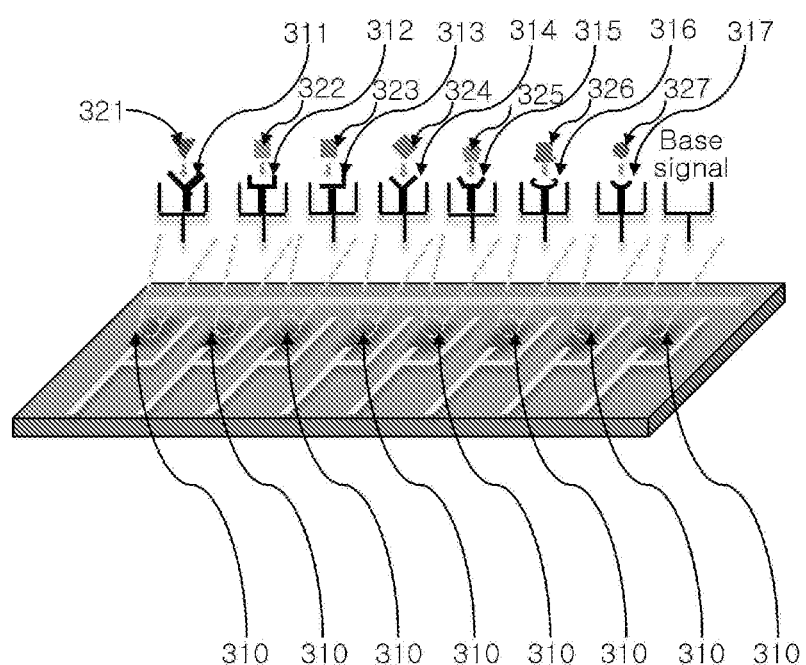
FIG. 3 presents a perspective schematic diagram of an embodiment of present disclosure, illustrating individual sensing electrodes being configured to detect different analytes.

FIG. 3 illustrates a perspective schematic representation of one embodiment of an electrochemical biosensor 100, wherein each individual sensing electrode 310 is coated with specific analyte probes 311-317 (e.g., antibody) such that different analytes 321-327 (e.g., proteins) can bind to the different probes 311-317 (e.g., by protein-protein interaction, DNA DNA hybridization and/or other intermolecular binding) that are immobilized on the individual sensing electrode 310. The term "immobilized" means binding a specific analyte probe (e.g., 311) to the surface of the sensing electrode 310, for example, by binding the probe to the electrode surface by covalent bonding, hydrogen bonding, ionic bonding, and/or Van der Walls forces. In one preferred embodiment, the electrochemical biosensor comprises a plurality of electrodes 310 capable of sensing very low amounts of analytes (e.g., less than 1000 fM in concentration, less than 500 fM in concentration, less than 100 fM in concentration, less than 10 fM in concentration and/or less than 1 fM in concentration).

Figure 4:
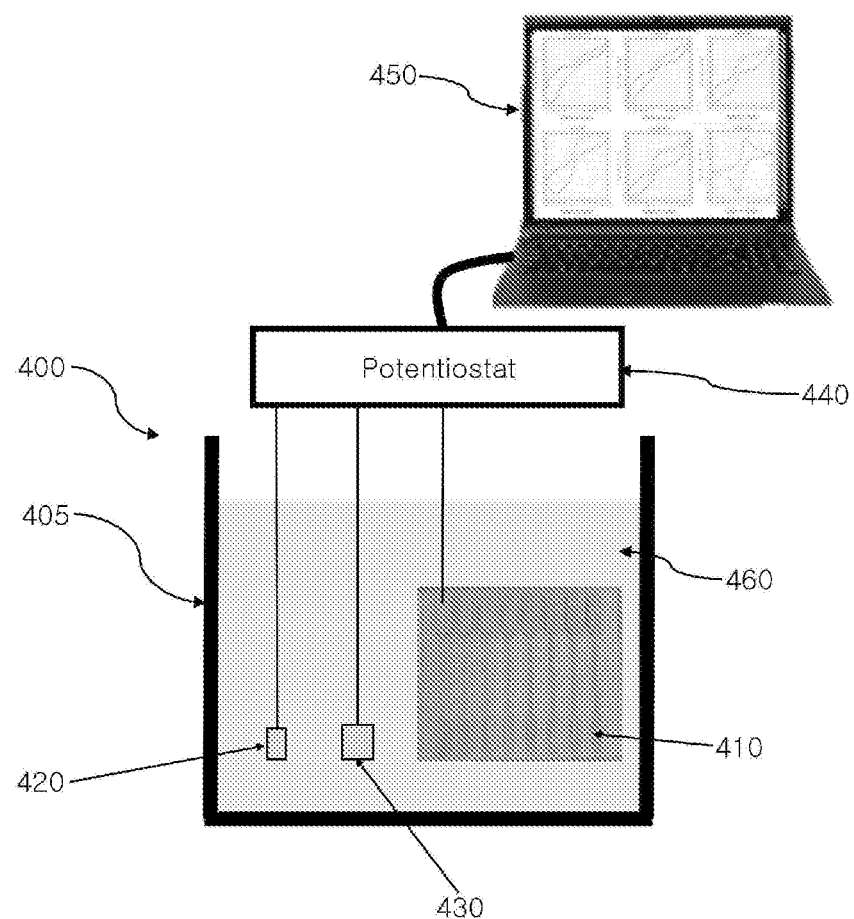
FIG. 4 presents a schematic diagram of how a biosensor may be used in conjunction with a potentiostat and an electronic device to detect analytes in a sample.

FIG. 4 illustrates a schematic representation of how one preferred embodiment of an electrochemical biosensor 410 may be used in conjunction with a potentiostat 440 and an electronic device 450 to detect analytes in a sample. In one embodiment, a user (e.g., a consumer, a laboratory personnel, a nurse, a doctor, a computer system, a machine or robotic device that uses the present disclosure as a component or step) may use the present disclosure to measure analytes era samples by performing the following steps: (1) applying test samples to the sensing electrodes to allow binding of analytes to analyte probes; (2) rinsing the sensing electrodes to remove unbound and/or non-specifically bound molecules (analytes and/or non-analytes) from the sensing electrode, (3) performing electrochemical measurements and analysis on the sensing electrodes.

A preferred embodiment of the present disclosure uses cyclic voltammetry to measure electrochemical properties of an analyte in solution, as shown in FIG. 4, FIG. 4 is a schematic diagram of how a biosensor may be used to detect analytes in a sample.

In such an embodiment, an electrochemical biosensor (working electrode) 410 is used in conjunction with an electrochemical chamber 400, a potentiostat 440, and an electronic devices 450 such as a computing device (e.g., personal computer, server, laptop, smartphone, purpose-built electronic device, and/or any other device that may be capable of receiving and analyzing electrical signals from the present disclosure). The electrochemical chamber 400 comprising a reservoir 405, a reference electrode 420, a counter electrode 430, and working electrode (the working electrode being a component of the electrochemical biosensor) 410. The reference electrode 420, counter electrode 430 and working electrode 410 may be submerged in a solution of electrolyte 460 such that when an electrical excitation is applied to the system 400, the electrical excitation causes chemical responses (e.g., oxidation and/or reduction reactions) that can be detected and analyzed by an electronic device 450. More specifically, when a current is applied to flow between the working electrode 410 and counter electrode 430, electric potential of the working electrode 410 relative to the reference electrode 420 can be controlled by the potentiostat 440. In this instance, the electric potential between the working electrode 410 and the reference electrode 420 can be measured accurately, irrespective of electric current resulting from electrode reaction. A person skilled in the art will appreciate that other alternative electrochemical measurement methods may also be adopted to the present disclosure, and thus are within the scope of the present disclosure.

Figure 5A:
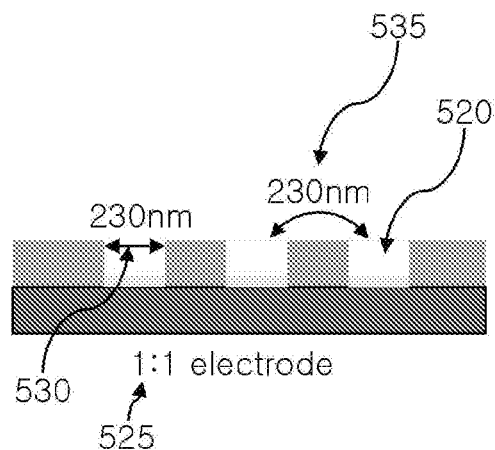
FIGS. 5A-5C present schematic diagrams illustrating exemplary pitch ratios of nanowells on biosensor sensitivity.
Figure 5B:
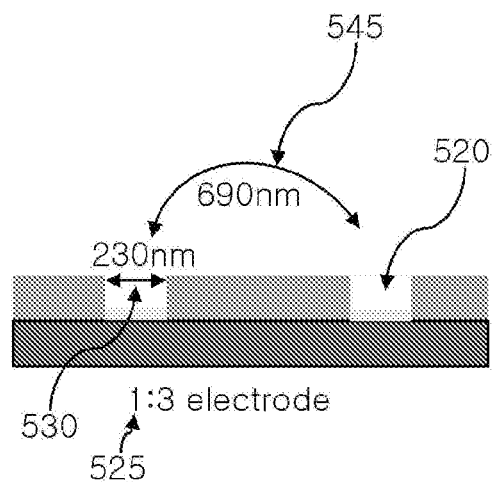
Figure 5C:
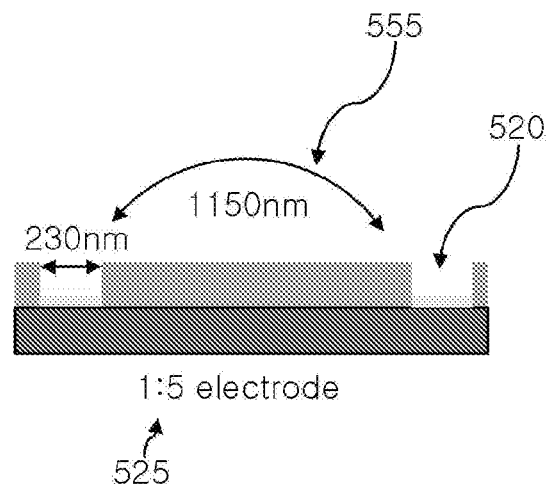

FIGS. 5A-5C illustrate cross sectional schematic representation of various embodiments of the present disclosure having different distribution of nanowells 520 on a sensing electrode 500. Distribution of the nanowells 520 is expressed in terms of pitch ratios 525 between neighboring nanowells 520. A pitch ratio 525 is defined by the ratio between the opening diameter 530 of a nanowell 520 and the nearest distance 535, 545, 555 between two neighboring nanowells. Another illustration of the nearest distance 535, 545, 555 can be found in FIG. 5A, where the nearest distance between neighboring nanowells is shown to be 230 nm.

FIG. 5A illustrates a preferred embodiment where the pitch ratio 525 of the nanowells 520 is 1:1. In this embodiment, the nanowell 520 opening has a diameter 530 of 230 nm and the shortest distances 535 between the neighboring nanowells 520 is 230 nm. Hence, the ratio between the nanowell opening diameter 530 and the shortest distances 535 between the neighboring nanowells is 230 nm:230 nm, or 1:1. FIG. 5B illustrates yet another embodiment where the pitch ratio 525 is 1:3. In this embodiment, the nanowell 520 opening has a diameter 530 of 230 nm and the shortest distance 545 between the neighboring nanowells 520 is 690 nm. Hence, the ratio between the nanowell opening diameter 530 and the shortest distance 545 between neighboring nanowells is 230 nm:690 nm, or 1:3. FIG. 5C illustrates still yet another embodiment where the pitch ratio 525 is 1:5. In this embodiment, the nanowell 520 opening has a diameter 530 of 230 nm and the shortest distance 550 between the neighboring nanowells 520 is 1150 nm. Hence, the ratio between the nanowell opening diameter 530 and the shortest distance 550 between neighboring nanowells is 230 nm: 1150 nm, or 1:5, Another embodiment of the shortest distance (535, 545, 555) is shown in FIGS. 5A, 5B and 5C. FIG. 5B indicates that the shortest distance between neighboring nanowells is 230 nm.

A person skilled in the art will recognize that, as discussed earlier in the present disclosure, that these are exemplary embodiments, and other sizes of nanowells and/or pitch ratios are also within the scope of the present disclosure. For example, the nanowell opening diameter can be approximately 1000 nm, approximately 500 nm, approximately 100 nm, approximately 50 nm, approximately 2.0 nm or less than 20 nm. Similarly, pitch ratios can range from any ratio between 100:1 to 1:100, including 50:1, 10:1, 5:1, 3:1, 1:1, 1:3, 1:5, 1:10 or 1:50. In addition, although the nanowell distribution in the embodiments are in a grid-like uniform patterns, other similar patterns or non-uniform distribution of nanowells and/or other similar, equivalent, and/or further improvements to the arrangement that can further improve sensitivity and/or specificity of the present invention are within the scope of the present disclosure.

Figure 6A:
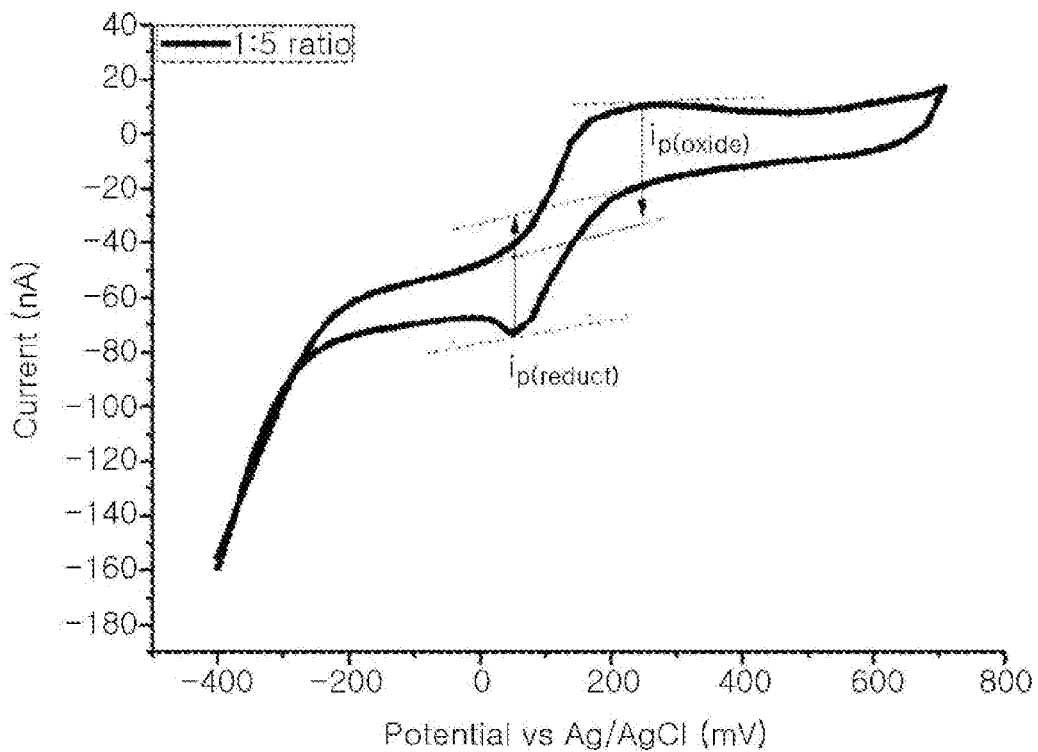
FIGS. 6A-6C present representative cyclic voltammetry (CV) analysis data illustrating the effect of varying pitch ratios on biosensor sensitivity.
Figure 6B:
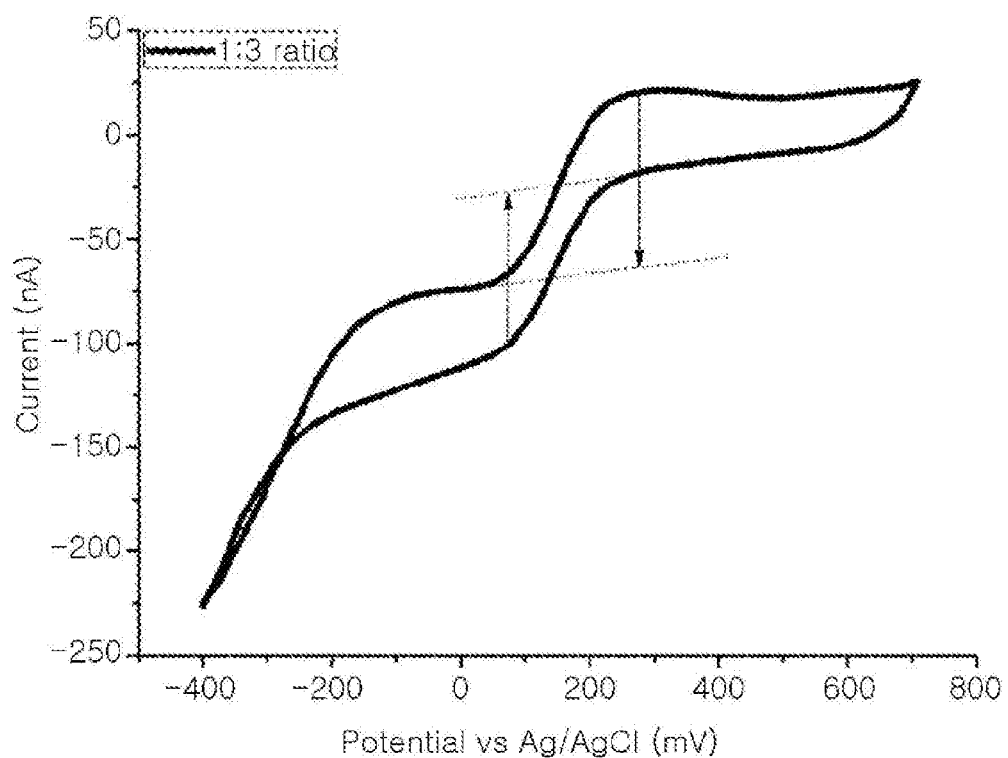
Figure 6C:
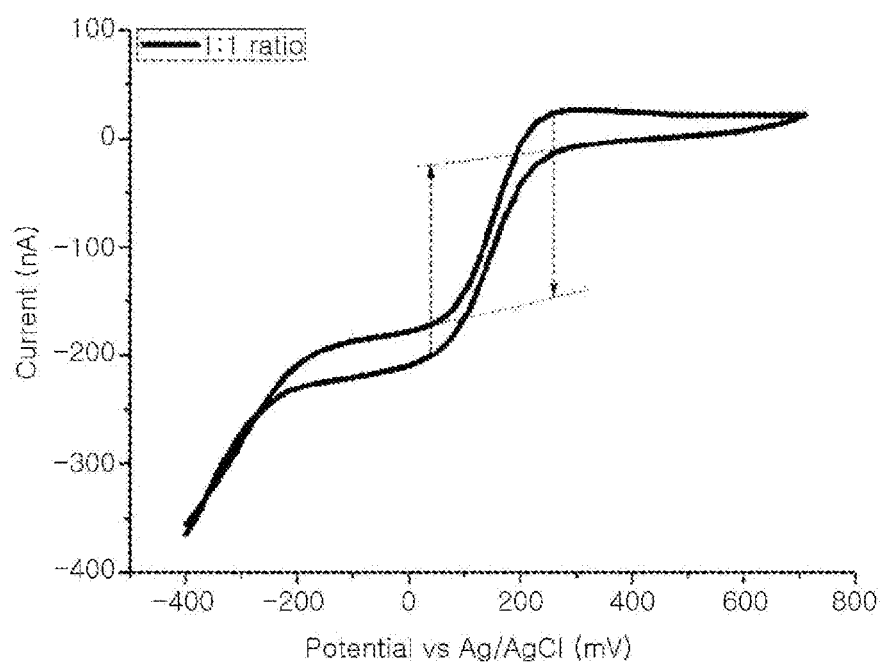

FIGS. 6A-6C illustrate differences in sensitivity of electrochemical biosensors having different nanowell pitch ratios (i.e., distances between neighboring nanowells). Generally, varying pitch ratios between nanowells results in changes in detection sensitivity. Specifically, cyclic voltammetry measurement of the present invention was performed wherein FIG. 6C shows highest sensitivity (cathodic peak of $1.75 \times 10^{-7}$ nA) for biosensors having nanowell pitch ratio of 1:1, compared to FIG. 6A (cathodic peak of $4.4 \times 10^{-8}$, biosensors having nanowell pitch ratio of 1:5) or FIG. 5B (cathotic peak of $7.9 \times 10^{-8}$, biosensors having nanowell pitch ratio of 1:3). One skilled in the art will appreciate that both nanowell 420 opening sizes, pitch ratio, and/or other dimensional, topographical, and/or physical attributes of the nanowells may affect sensitivity of the present disclosure, and variable configurations of nanowells is within the scope of the present disclosure.

Figure 7:
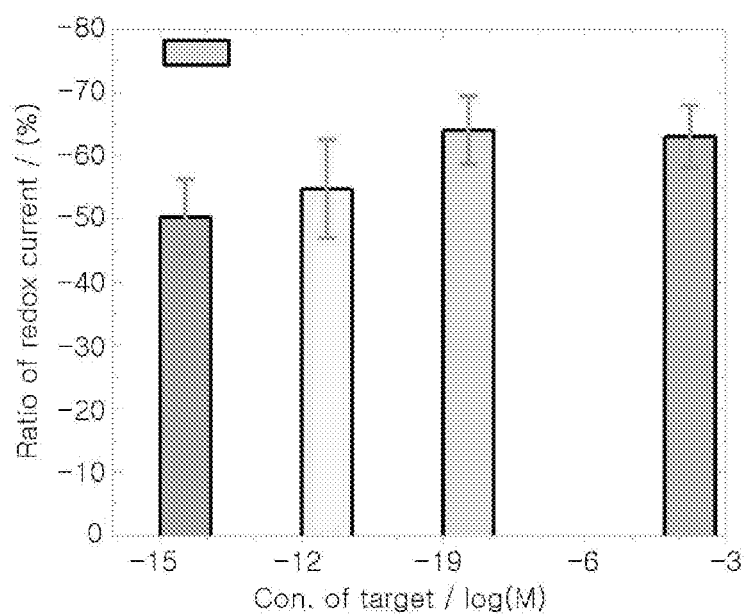
FIG. 7 presents a representative data illustrating detection of varying concentration of DNA analytes in a solution using an embodiment of present disclosure.

FIG. 7 shows representative data showing the ratio of redox current measured by an embodiment of the present disclosure to detect different concentrations of DNA analytes. Detection of the presence of analytes in samples having analyte concentrations ranging from mM ($10^{-4}$ M) range to fM ($10^{-15}$ M) range was performed by measuring changes in redox current, represented in percentages. This example illustrates that an embodiment of the present disclosure can detect fM range of DNA analytes by detecting statistically significant ratio of redox current.

Detailed Description of Biosensor Manufacturing Methods

Figure 8:
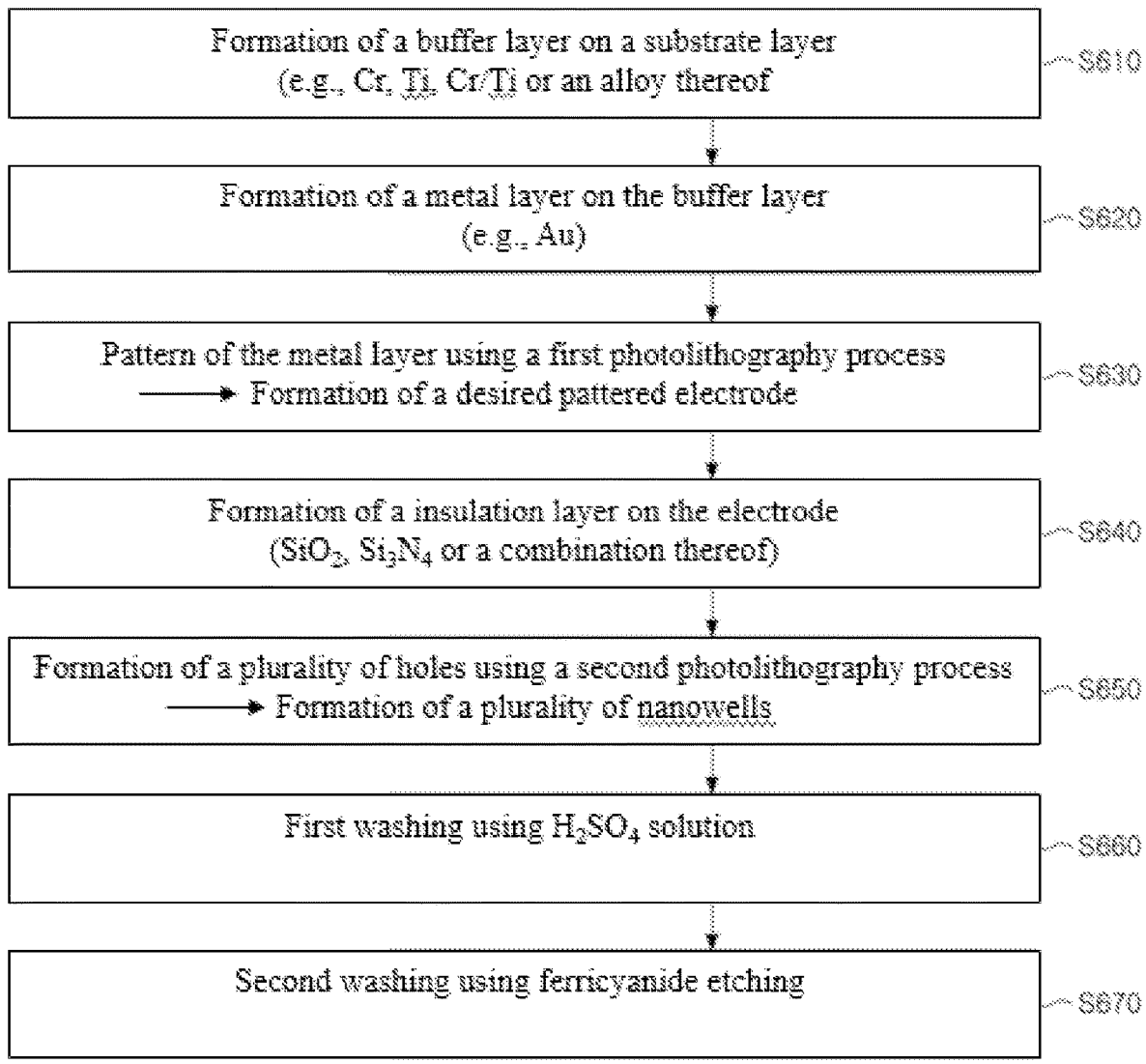
FIG. 8 presents a flow chart illustrating a manufacturing method of a biosensor.

Generally, the present disclosure is directed to methods of production of electrochemical 2.5 biosensors comprising steps for removing and/or reducing impurities from the electrochemical biosensors. In certain embodiments, the present disclosure comprises steps of removing impurities from surfaces of electrodes of electrochemical biosensors. For example, FIG. 8 and FIGS. 9A-9H show some embodiments of the present invention of the manufacturing methods of electrochemical sensors that minimize contamination of biosensors (e.g., electrode surfaces) with impurities. FIG. 8 is a flow chart illustrating an embodiment of manufacturing methods of biosensors and FIGS. 9A-9H are schematic diagrams illustrating some embodiments of major steps of the manufacturing method of the biosensor.

In one embodiments of the invention, the biosensor manufacturing method comprises forming a buffer layer on a substrate layer (S610) and forming a metal layer on the buffer layer (S620). Specifically, as described in FIG. 9A, the buffer layer 220 and the metal layer 230 are sequentially formed on the substrate layer 210.

The substrate layer 210 may be made of glass, silicone, silicon dioxide (e.g., quartz), and/or borosilicate used in semiconductor manufacturing. The buffer layer 220 provides enhanced bonding of the metal layer 230' and the substrate layer 210. For example, the buffer layer 220 comprises titanium (Ti), chromium (Cr), and/or an alloy thereof. In certain embodiments, Cr/Ti can be used. The metal layer 230' is provided for the electrode and may include, for example, gold (Au). As the deposition process, various deposition processes such as sputtering and electron beam deposition may be used.

The method of the present invention further comprises forming a desired pattered electrode 230 by patterning the metal layer 230' using a first photolithography process. Specifically, above process can be performed by the process shown in FIGS. 9B and 9C.

Figure 9A:
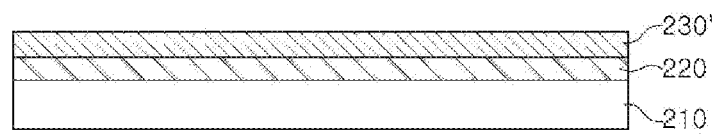
FIGS. 9A-9H present schematic diagrams illustrating major steps of the manufacturing method of the biosensor.
Figure 9B:
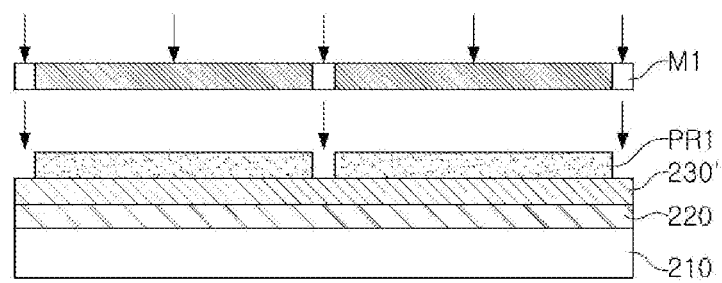
Figure 9C:
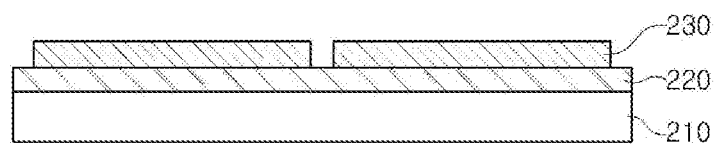
Figure 9D:
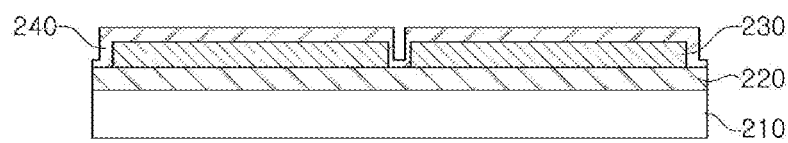

Referring to FIG. 9B, a photoresist material is coated on the metal layer 230', selective exposure is performed using an exposure apparatus such as a KrF stepper and a reticle M1 having a desired pattern, thereby forming a desired first photoresist pattern PR1. Next, as shown in FIG. 9C, the electrode 230 having the desired pattern can be formed by selectively removing the metal layer 230' using the first photoresist pattern PR1 as a mask.

As shown in FIG. 9B, the insulator layer 240 is formed on the electrode 230 (S640). The insulator layer 240 formed in this step is provided as a structure for forming a nanowell. In this embodiment, the inorganic insulator layer 240 having restoration and stability is used. For example, silicon nitride (Si3N4) or silicon oxide ($SiO_2$) may be used as the inorganic insulating layer 240. In particular, silicon nitride (Si3N4) or silicon oxide ($SiO_2$) may be preferably used rather than a polymeric material such as a photoresist, since a washing process such as a sulfuric acid washing and/or a ferricyanide etching is applied in a subsequent process.

Next, a plurality of holes can be formed in the insulator layer using the second photolithography process (S650). A plurality of holes formed in this process are provided as nanowells, and the electrode exposed on the bottom surface of the nanowells can be used as a sensing electrode. Specifically, this process can be performed by the process shown in FIGS. 9E and 9F.

Figure 9E:
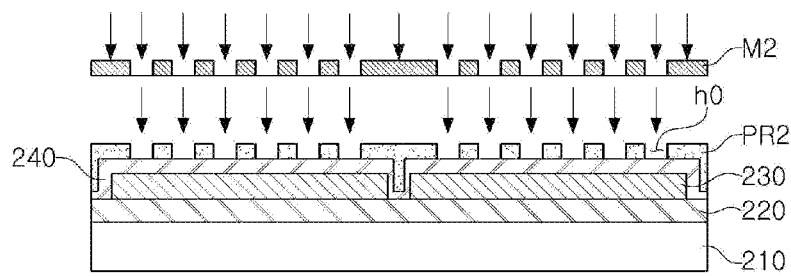
Figure 9F:
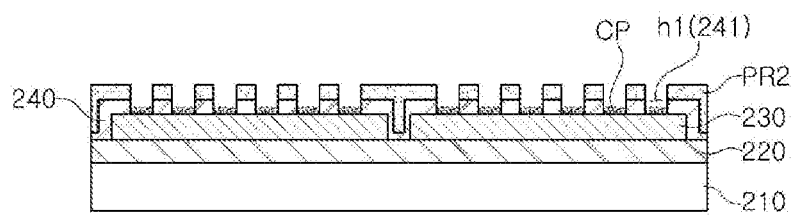

Referring to FIG. 9E, the photoresist material is coated on the insulator layer 240, selective exposure is performed using an exposure apparatus such as a reticle M2 having a nano sized hole pattern, similar to the previous step, thereby forming a desired second photoresist pattern PR2. Next, as shown in FIG. 9F, a desired hole h1 is formed by selectively removing the insulator layer 240 using the second photoresist pattern PR2 as a mask, wherein can be provided as the nanowell structure 241. However, impurities (CP) are generated in the process of forming the nanowells (241) exposing a part of the electrode (230) in the insulator layer (240). CP may remain on the surface of the electrode and greatly reduce the reliability of the biosensor.

Figure 9G:
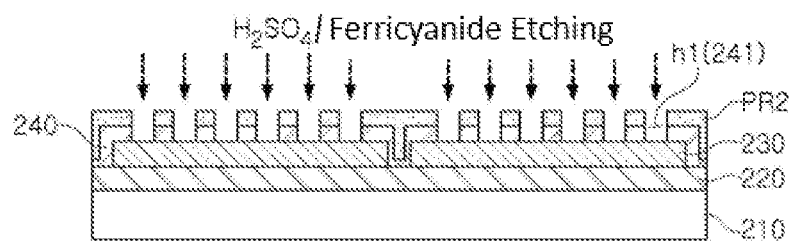

To solve this problem, various effective washing processes can be introduced after the formation of the nanowells, as shown in FIG. 9G. In addition to the washing process using a sulfuric acid solution, a ferricyanide etching process can also be used. Each process may be performed alone, but may be performed in parallel. Particularly, the most preferable effect can be expected by performing the ferricyanide etching (S670) after the sulfuric acid washing step. Specifically, the plurality of nanowells may be cleaned using a sulfuric acid ($H_2SO_4$) solution to remove impurities from the electrode exposed by the plurality of nanowells (S660). The sulfuric acid washing is performed by immersing the biosensor comprising the nanowell in a sulfuric acid and applying a voltage for a predetermined time. The applied voltage is in the range of 1.5 to 2.0 V, although not limited thereto, and can be performed for 1 to 5 minutes.

After the sulfuric acid washing, the plurality of nanowells can be cleaned using ferricyanide etching. The ferricyanide etching is performed by immersing the biosensor in a mixed solution of $K_3Fe(CN)_6$ and KCl and applying the voltage of 1.0 to 1.5 V.

Generally, an electrode made of gold is known to be unfavorable because of a reaction when a voltage of 1 V or higher is applied in the ferricyanide solution. However, by intentionally applying a voltage of 1.0-1.5 V, the surface of the electrode exposed on the bottom surface of the nanowell can be rapidly treated to effectively remove residual impurities and greatly improve the flatness of the electrode surface in the present invention. Although not limited thereto, the ferricyanide etching is performed at a temperature in the range of 15 to 25° C. for 1 to 10 seconds.

Figure 9H:
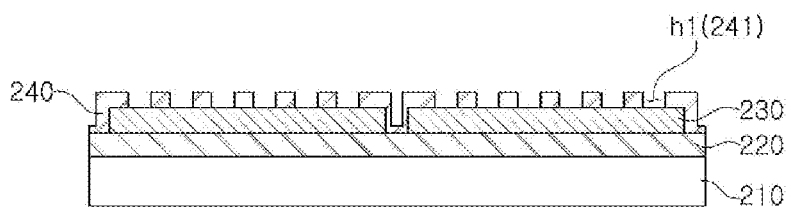

According to the FIG. 9H, the washing process removes the impurity (CP) from the electrode located on the bottom surface of the nanowell 241, planarizes the electrode region so that a high selectivity can be ensured.

Hereinafter, the present invention will be described in more detail with reference to the following Examples. However, these Examples are set forth to illustrate the present invention, and the scope of the present invention is not limited thereto.

EXAMPLE

Example 1. Effects of Washing Electrodes Having $Si_3N_4$ or Insulation Layer with $H_2SO_4$ and/or $K_3Fe(CN)_6$ A silicone substrate layer was prepared and a Cr layer with the 300 nm thickness and a Ti layer with the 10 nm thickness was deposited onto the silicone substrate layer as buffer layers. The Cr layer and the Ti layer were formed using the sputtering apparatus and the electron beam deposition apparatus, respectively. Sequentially, an Au layer with the 200 nm thickness was formed as the metal layer for the electrode using the electron beam deposition apparatus. Finally, a photoresist material is coated on the Au layer, and the photoresist pattern corresponding to a desired patterned electrode was formed using the exposure apparatus, KrF stepper, and a reticle. Using the photoresist pattern as a mask, Au was selectively removed in the Inductively Coupled Plasma (ICP) etching apparatus and, with the same pattern, the Ti layer was selectively removed. The photoresist pattern was removed by immersing tier 3-4 minutes in an ultrasonic beaker using acetone.

Next, to form an insulation layer for a nanowell array, a $Si_3N_4$ layer with the 150 nm thickness was deposited using plasma-enhanced chemical vapor deposition (PECVD), and, similar to the aforementioned photolithography process, the $Si_3N_4$ layer was selectively removed such that the holes had the opening diameter of a 230 nm with a pitch ratio of 1:1. However, the biosensors manufactured according to Example 1 underwent different washing processes as described in Table 1 below:

TABLE 1

| Example | Sulfuric Acid ($H_2SO_4$) Washing | Ferricyanide Etching |
|---|---|---|
| Example 1A | X | X |
| Example 1B | ○ | X |
| Example 1C | ○ | ○ |

The sulfuric acid washing was performed by immersing the biosensors into the $H_2SO_4$ solution and pretreating for 3 minutes at +1.8V before the CV analysis. The ferricyanide etching was performed by immersing the biosensors into the ferricyanide solution and treating $K_3Fe(CN)_6$ at the scan rate of 100 mV/s at the room temperature. A mixed solution of 5 mm $K_3Fe(CN)_6$ and 0.1M KCl solution was used as the ferricyanide solution. In addition, a solid Ag/AgCl bar (with 3M KCl) and a platinum wire were used as the reference and the counter electrodes. Specifically, the CV analysis, the sulfuric acid washing and the ferricyanide etching were carried out under conditions described in Table 2 below.

In one exemplary embodiment, the method of production of highly sensitive and highly selective electrochemical biosensors comprise a step of washing the electrodes with $K_3Fe(CN)_6$ solution. Preferably, the washing step is carried out under conditions described in Table 2.

In another exemplary embodiment, the method of production of highly sensitive and highly selective electrochemical biosensors comprise a step of washing the electrodes with $K_3Fe(CN)_6$ solution combined with the step of washing the electrodes with $H_2SO_4$. Preferably, these washing steps are carried out under conditions described in Table 2.

TABLE 2

Exemplary conditions for the cyclic voltammetry (CV) analysis, $H_2SO_4$ washing step and $Fe(CN)_6$ washing step.

| | CV | $H_2SO_4$ | $Fe(CN)_6$ |
|---|---|---|---|
| Init E (V) | −0.6 | 0 | −1.2 |
| High E (V) | 0.4 | 1.8 | 1.2 |
| Low E (V) | −0.6 | 0 | −1.2 |
| Init P/N | P | P | P |
| Scan Rate (V/s) | 0.1 | 0.1 | 0.1 |
| Segment | 5 | 4 | 3 |
| Sample Interval (V) | 0.01 | 0.01 | 0.01 |
| Quet Time (Sec) | 2 | 2 | 2 |
| Sensitivity (A/V) | 1e−5 | 1e−4 | 0.001 |

In certain embodiments, the $Fe(CN)_6$ washing step is performed using 5 mM $K_3Fe(CN)_6$ and 0.1M KCl solution.

In certain embodiments, the electrode is pretreated for 3 minutes at +1.7-1.8 V in $H_2SO_4$ solution prior to CV analysis. The electrochemical data are then measured in solutions containing $K_3Fe(CN)_6$ at a scan rate of 100 mV/s, at room temperature.

In certain embodiments, a solid Ag/AgCl bar (with 3M KCl) and a platinum wire are used as the reference and counter electrode.

In certain embodiments, the methods of production disclosed herein results in electrodes of the biosensors having improved electrochemical properties. In one preferred embodiment, the electrochemical properties are measured using cyclic voltammetry analysis.

In certain embodiments, the scan cycle of the $Fe(CN)_6$ washing step comprises one cycle or two cycles. In certain other embodiments, the scan cycle of the $Fe(CN)_6$ washing step comprises more than two cycles.

It is well known in the art that $Fe(CN)_6$ washing conditions comprising application of electric current with a voltage of greater than 1 V is likely to adversely affect the surface integrity of the electrodes. However, in certain embodiments of the present disclosure, electric current with a voltage of greater than 1 V is applied for a short duration to yield Unexpectedly advantageous results, such as removal of impurities and enhanced electrochemical properties of electrodes of biosensors. In certain other embodiments, similar unexpectedly advantageous results can occur with $Fe(CN)_6$ washing conditions comprising application of electric current with a voltage of 0.9-1.5 V, 1.0-1.4 V, 1.1-1.3 V, or 1.15-1.25 V.

As described previously, electrochemical biosensors comprising insulation layers having nanowells can consist with materials which does not react during $Fe(CN)_6$ washing step, such as inorganic materials. Some embodiments of the present disclosure are especially well suited for electrochemical biosensors that comprise insulation layers made of $Si_3N_4$ or $SiO_2$. In some embodiments, the present disclosure is not well suited for photolithography of electrochemical biosensors comprising insulation layers having nanowells- (due to weak bonding between gold and the insulation layers.

In some embodiments, the present disclosure may be adapted to be used with phosphate-buffered saline solution, for example, with respect to the ferricyanide etching step.

The nanowell array of the resultant biosensors, e.g., the biosensors manufactured by Examples 1A-1C, was photographed by SEM, and the CV analysis was carried out for each biosensor.

In some embodiments, the present disclosure may be adapted to be used using methylene blue (i.e., methylthioninium chloride) as washing solution, either in addition to the ferricyanide and/or $H_2SO_4$ washing, or without the ferricyanide and/or $H_2SO_4$ washing.

Effects of Washing Electrodes Having $Si_3O_4$ or $SiO_2$ Insulation Layer with $H_2SO_4$ and/or $K_3Fe(CN)_6$, as Shown in FIGS. 10A-15B.

Figure 10A:
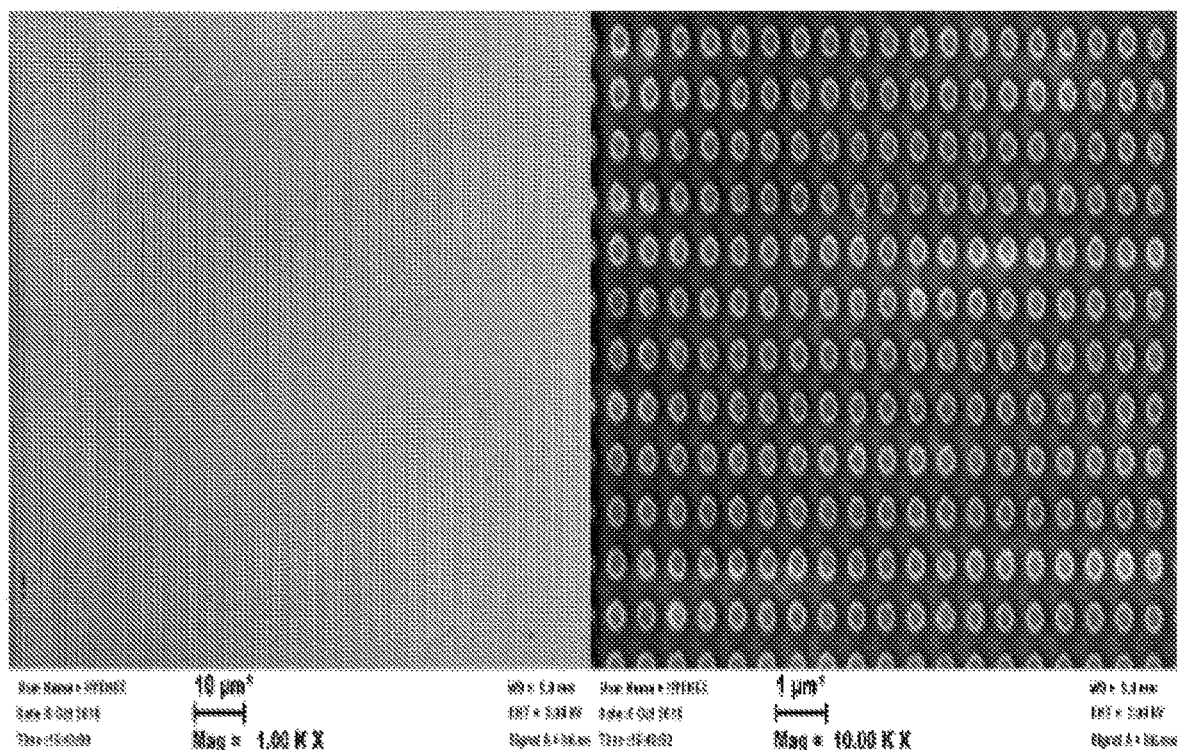
FIGS. 10A-10B present representative scanning electron micrograph (SEM) and cyclic voltammetry (CV) analysis data for biosensor electrodes comprising $Si_3N_4$ insulation layer, where the biosensor is produced without $H_2SO_4$ washing or ferricyanide etching (or washing) step.
Figure 10A:
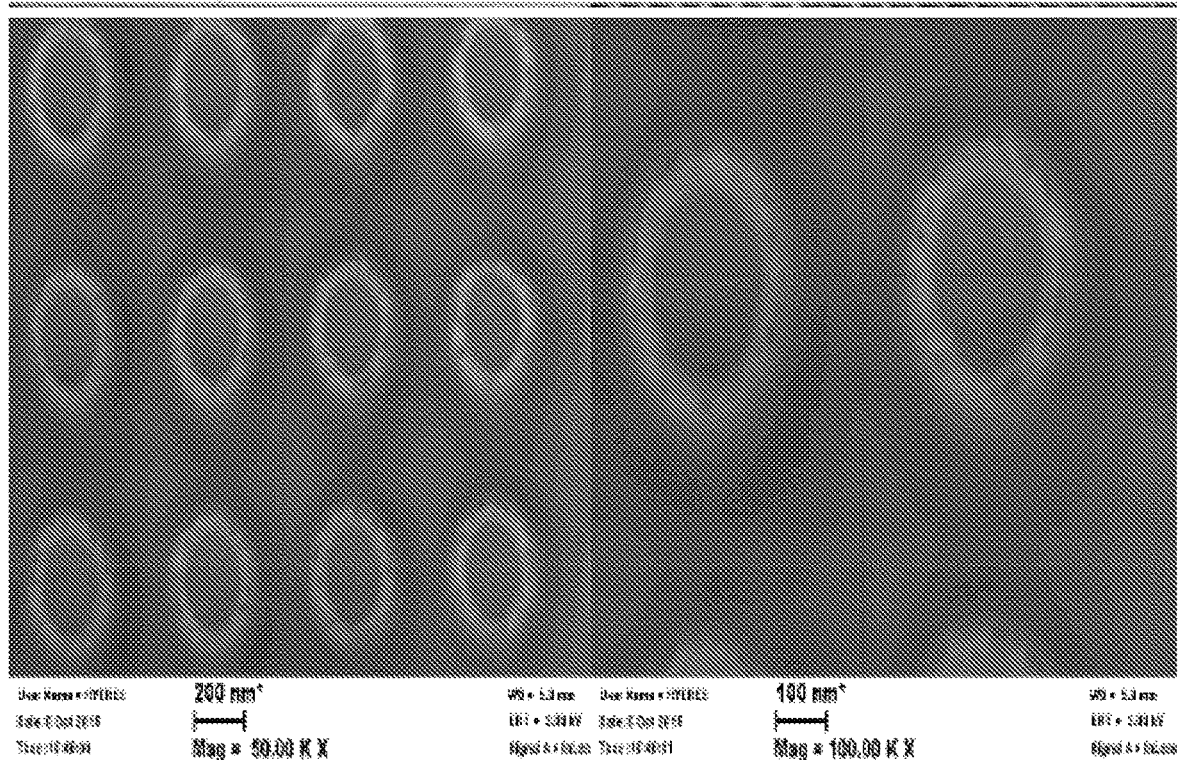

FIG. 10A shows SEM image of a nanowell array surface formed from $Si_3H_4$ resist layer. In this example, cleaning by $H_2SO_4$ or ferricyanide etching are not performed. Nanowells in uniform arrays are shown. As shown in the lower panel, each nanowell is approximately 230 nm in diameter and the nanowells are spaced with a pitch ratio of 1:1 (the scale bar in the SEM picture: 200 nm).

Figure 10B:
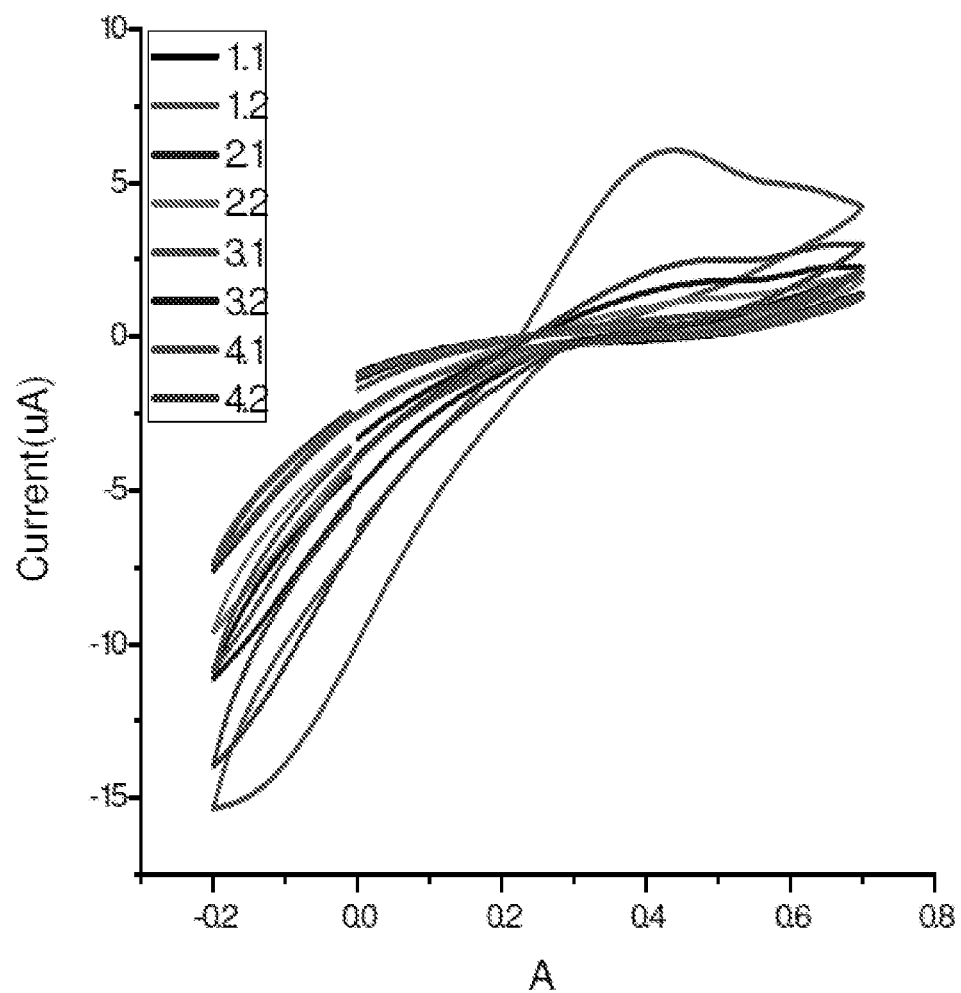

FIG. 10B shows CV analysis data for nanowell array electrodes exemplified in FIG. 10A.

Figure 11A:
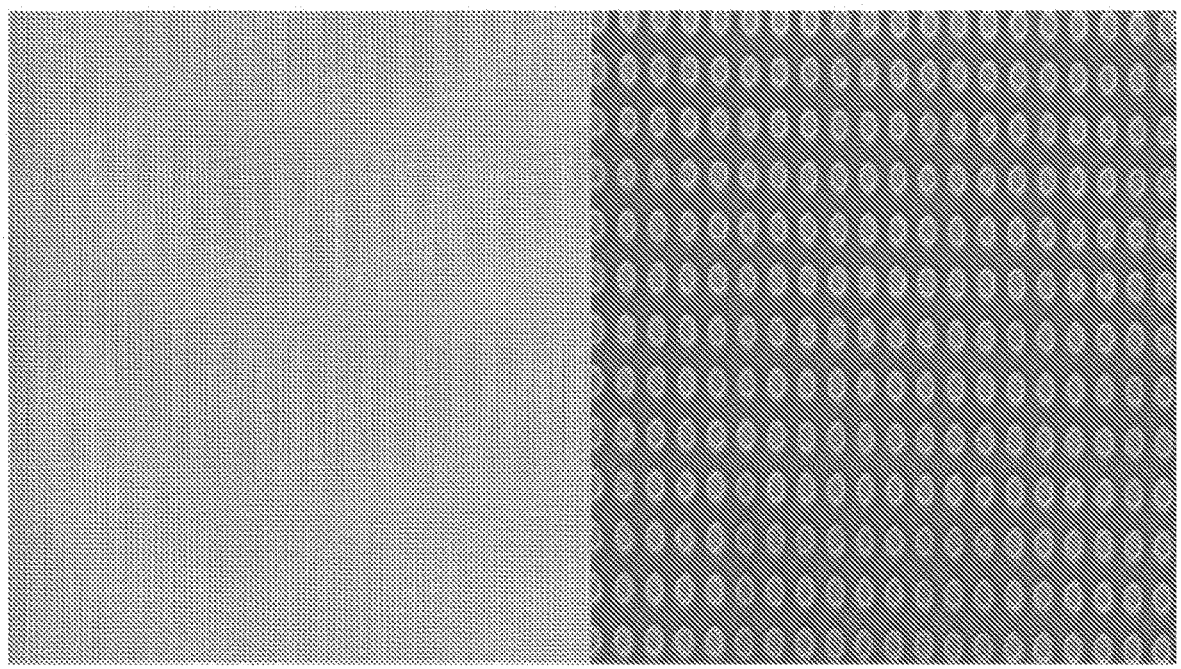
FIGS. 11A-11B present representative SEM and CV analysis data for biosensor electrodes comprising $Si_3N_4$ insulation layers, where the biosensor is produced using a method comprising $H_2SO_4$ washing step.
Figure 11A:
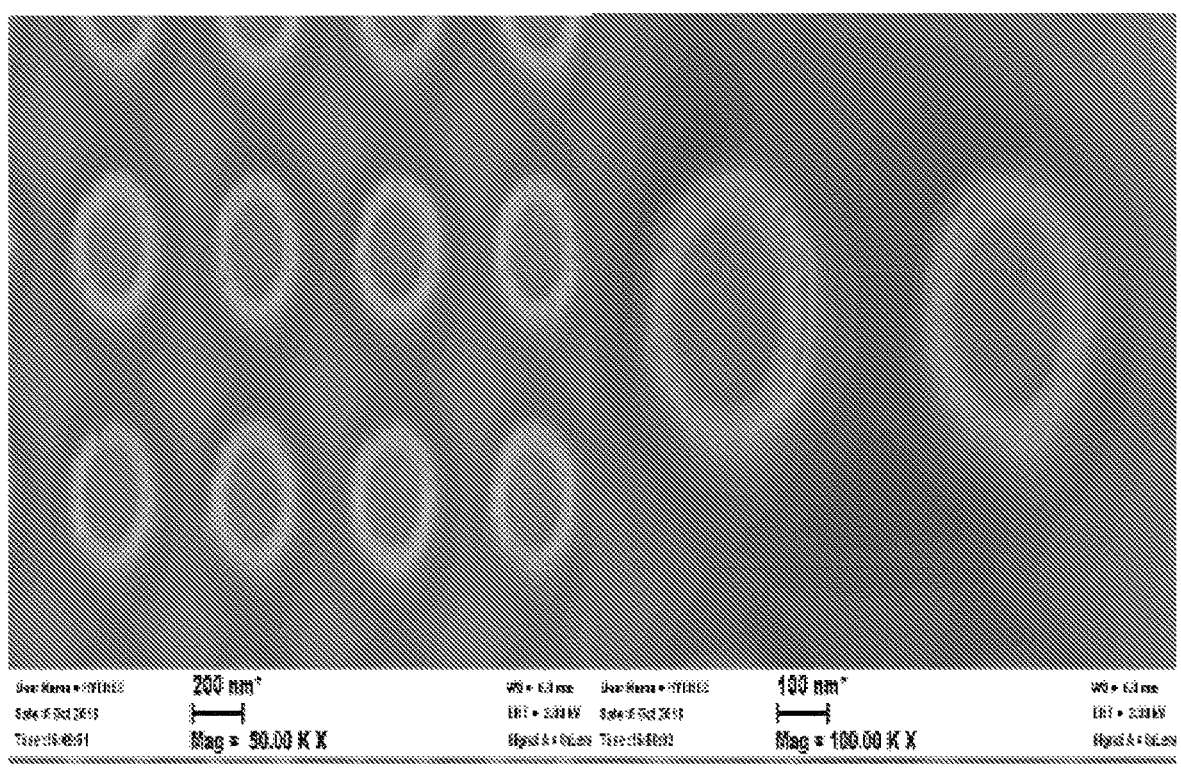

FIG. 11A shows SEM image of a nanowell array surface formed from $Si_3N_4$ resist layer. In this example, $H_2SO_4$ washing step was performed. Nanowells in uniform arrays are shown. As shown in the lower panel, each nanowell is approximately 230 nm in diameter and the nanowells are spaced with a pitch ratio of 1:1 (the scale bar in the SEM picture: 200 nm).

Figure 11B:
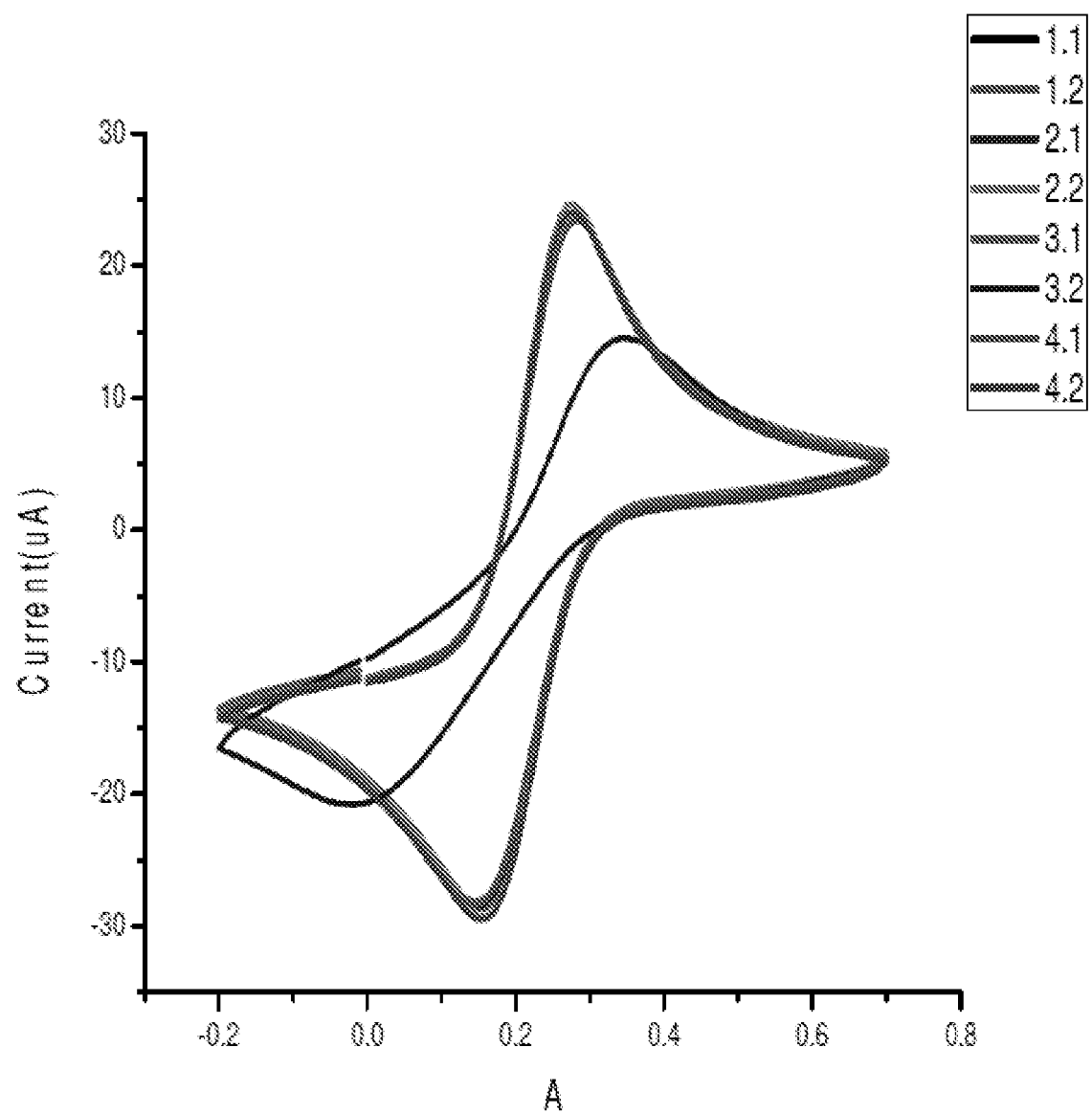

FIG. 11B shows CV analysis data for nanowell array electrodes exemplified in FIG. 11A.

Figure 12A:
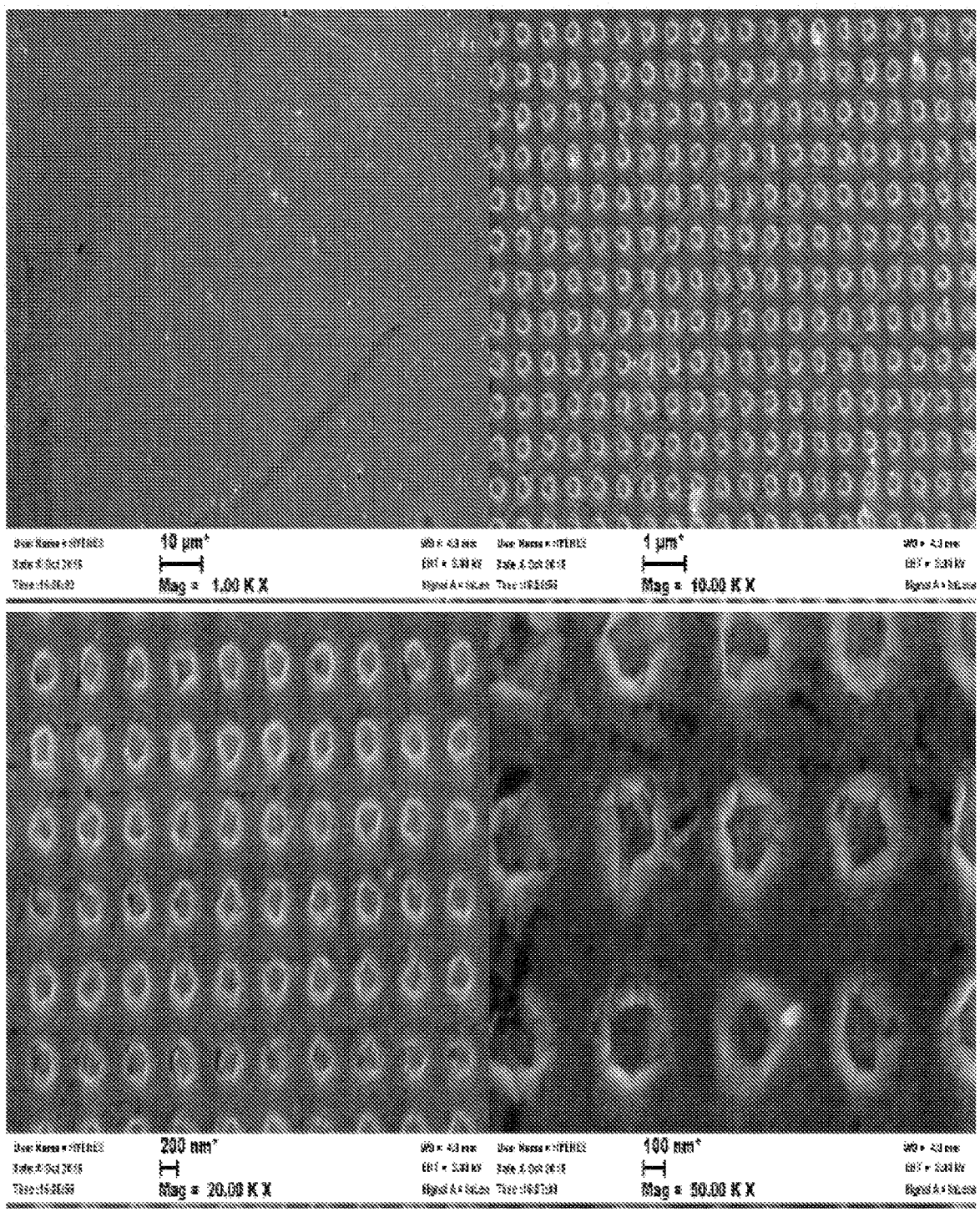
FIGS. 12A-12B present representative SEM and CV analysis data for biosensor electrodes comprising $Si_3N_4$ insulation layers, where the biosensor is produced using a method comprising $H_2SO_4$ washing step and ferricyanide etching (or washing) step.

FIG. 12A shows SEM image of a nanowell array surface formed from $Si_3N_4$ resist layer. In this example, $H_2SO_4$ washing step and ferricyanide etching (or washing) step were performed. Nanowells in uniform arrays are shown. As shown in the lower panel, each nanowell is approximately 230 nm in diameter and the nanowells are spaced with a pitch ratio of 1:1 (the scale bar in the SEM picture: 200 am).

Figure 12B:
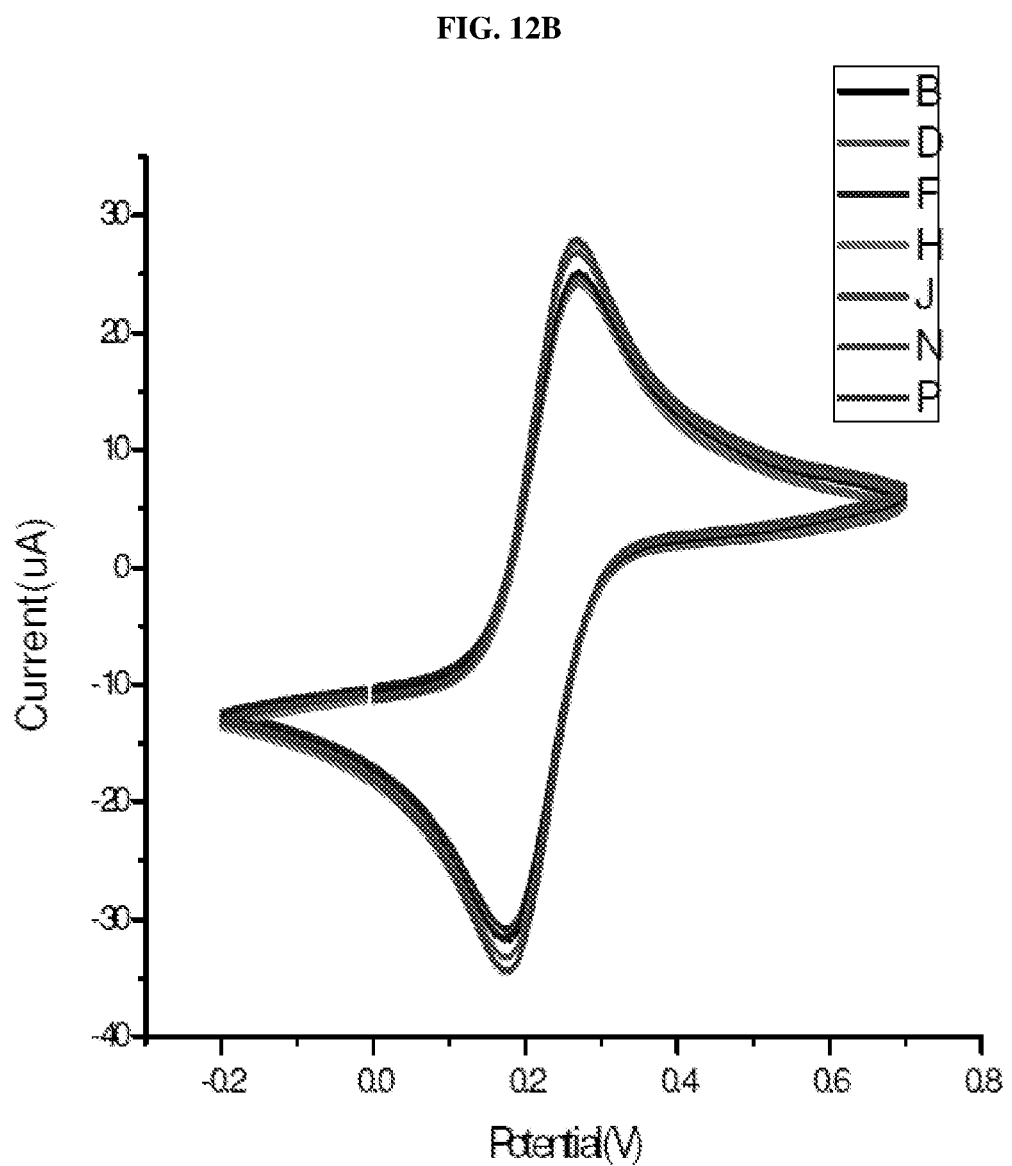

FIG. 12B shows CV analysis data for nanowell array electrodes exemplified in FIG. 12A.

Figure 16A:
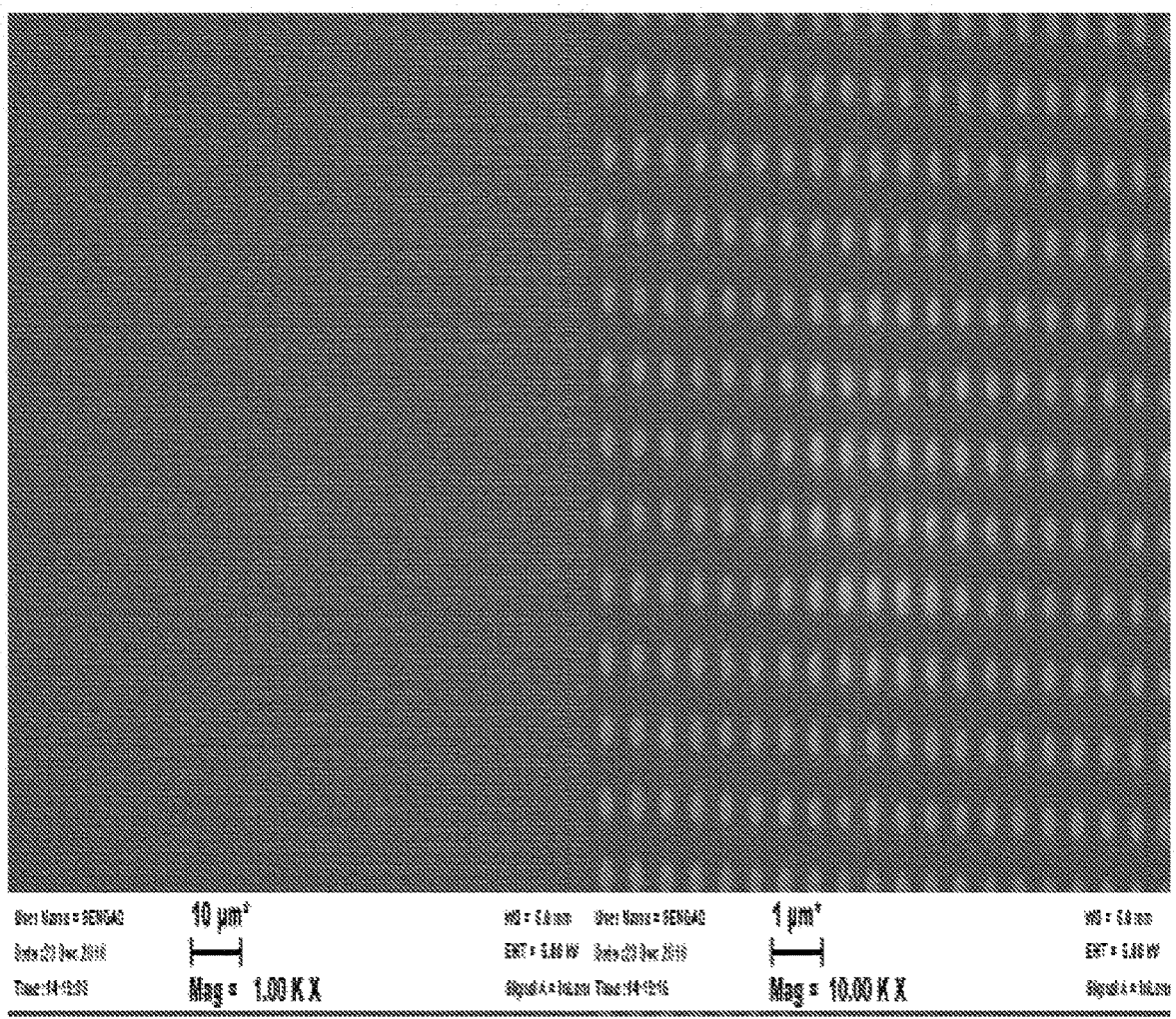
FIGS. 16A-16B present representative SEM and CV analysis data for biosensor electrodes made using photolithography, where the biosensor is produced without $H_2SO_4$ washing or ferricyanide etching (or washing) step.

The CV analysis data reveal lack of well-defined redox peaks, as shown in FIGS. 10A and 16A, suggesting presence of significant impurities on the electrode surfaces.

Figure 13A:
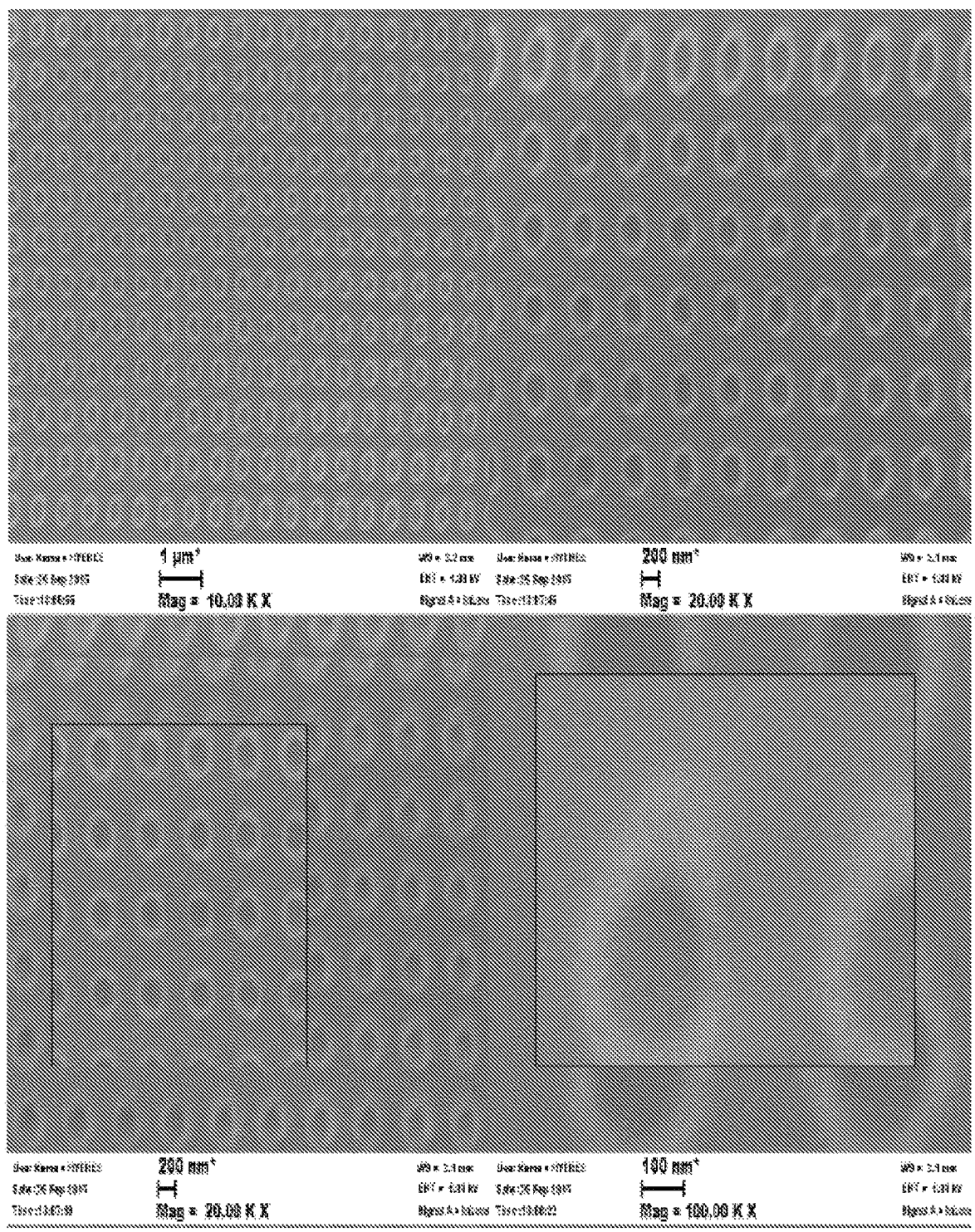
FIGS. 13A-13B present representative SEM and CV analysis data for biosensor electrodes comprising $SiO_2$ insulation layer, where the biosensor is produced without $H_2SO_4$ washing or ferricyanide etching (or washing) step.

The CV analysis data also reveal normal oxidation current peak but irregular reduction current peak in FIG. 13A, suggesting presence of some impurities on the electrode surfaces.

Figure 16B:
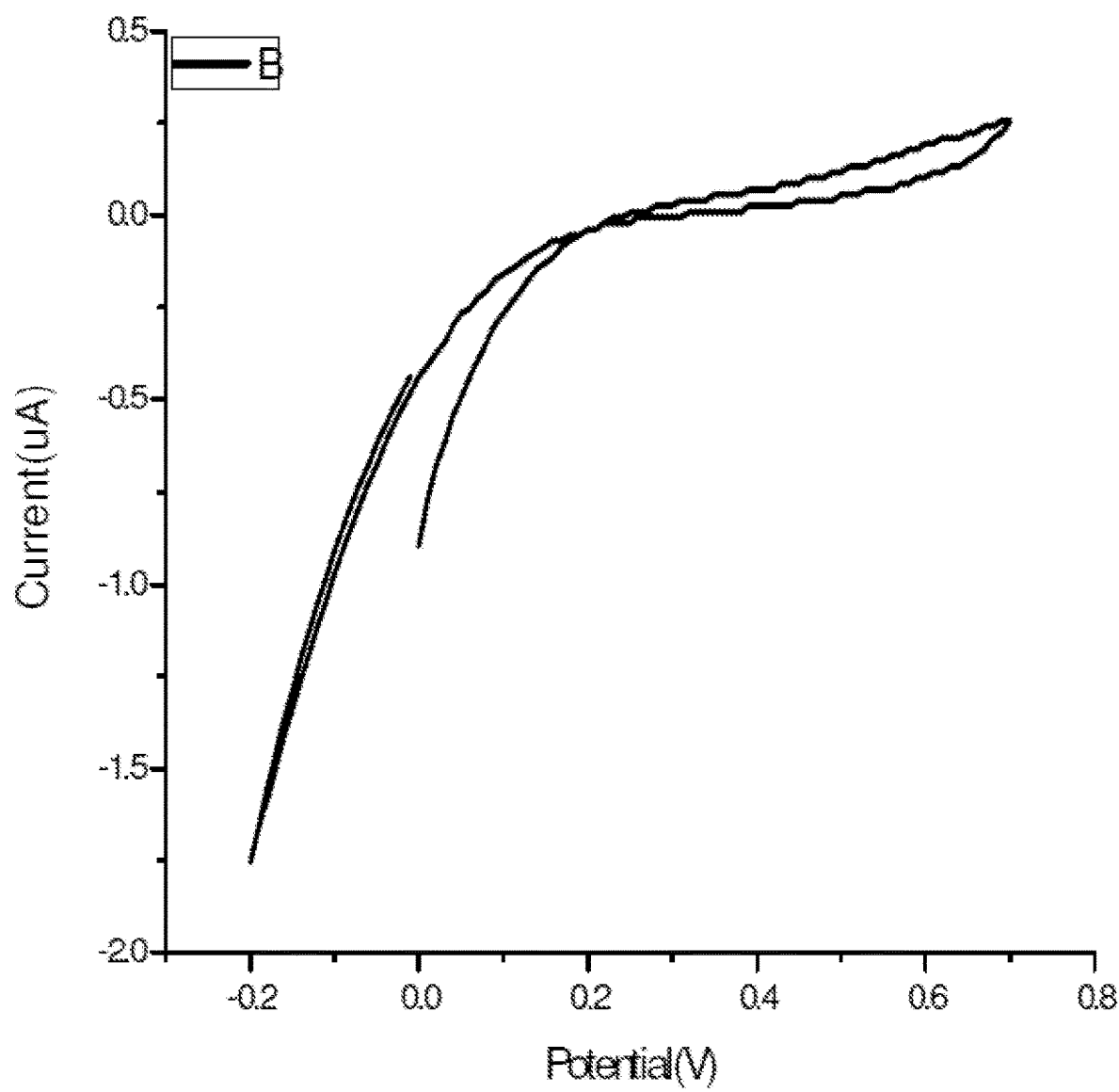
Figure 17A:
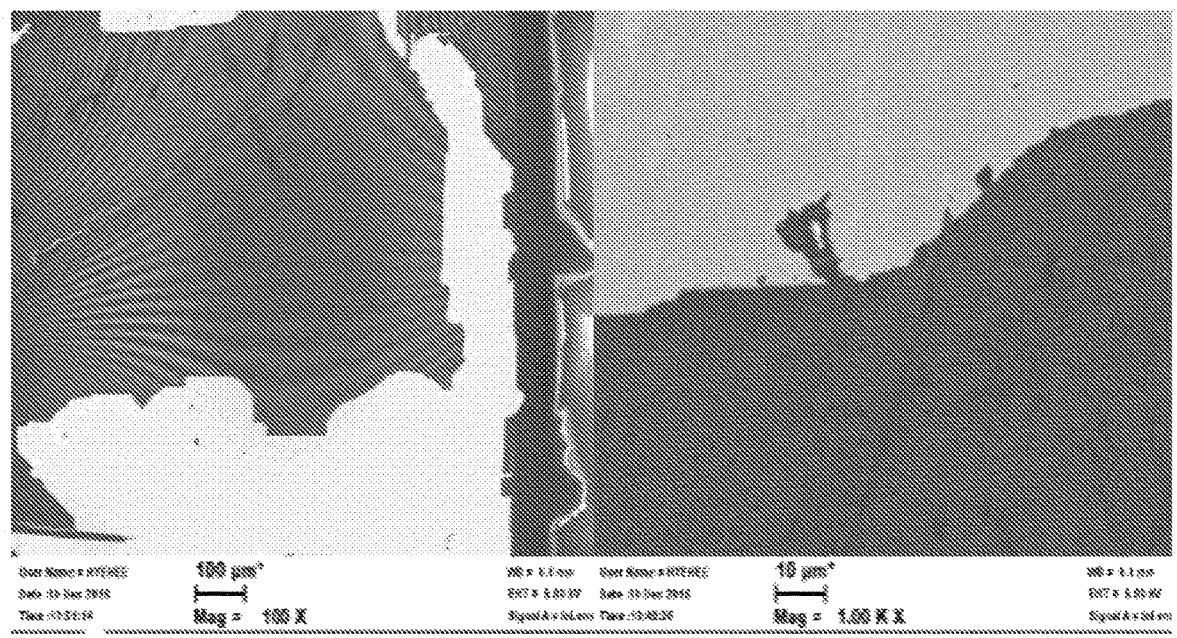
FIGS. 17A-17B present representative SEM and CV analysis data for biosensor electrodes made using photolithography, where the biosensor is produced using method comprising $H_2SO_4$ washing step.
Figure 17A:
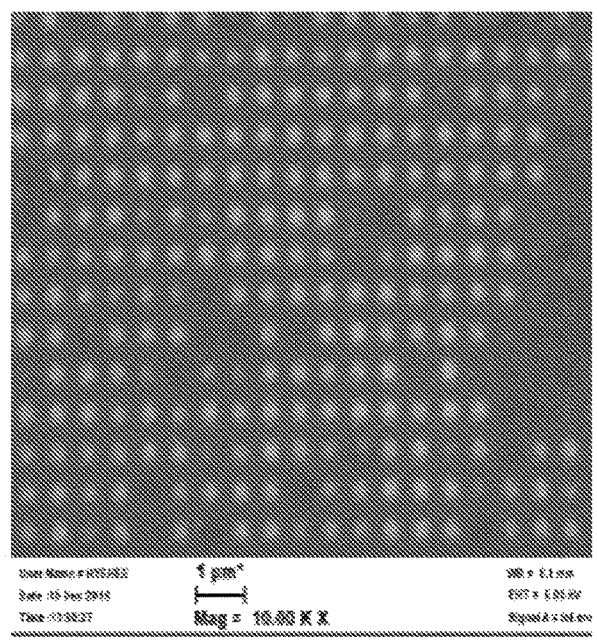
Figure 17B:
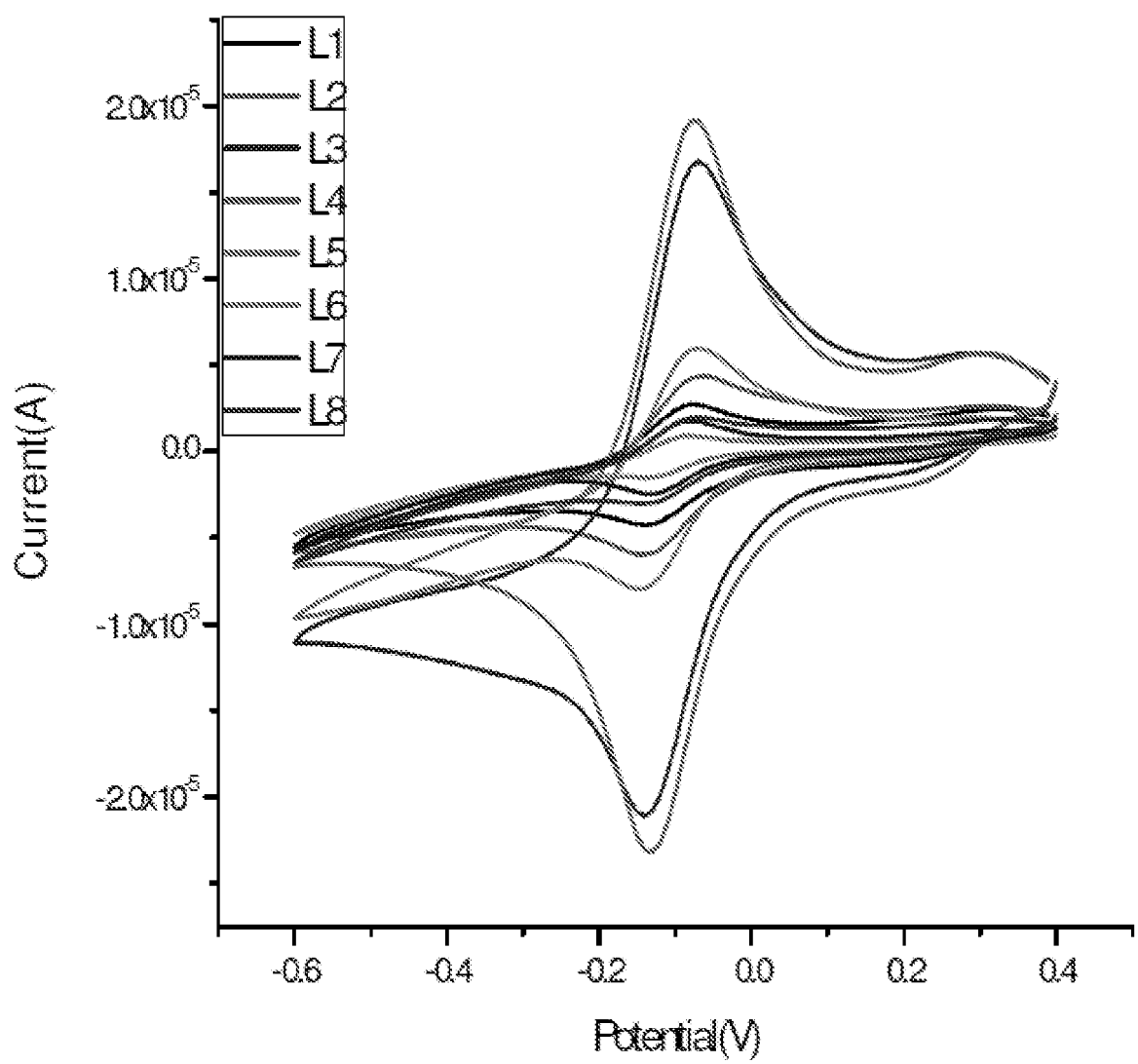
Figure 18A:
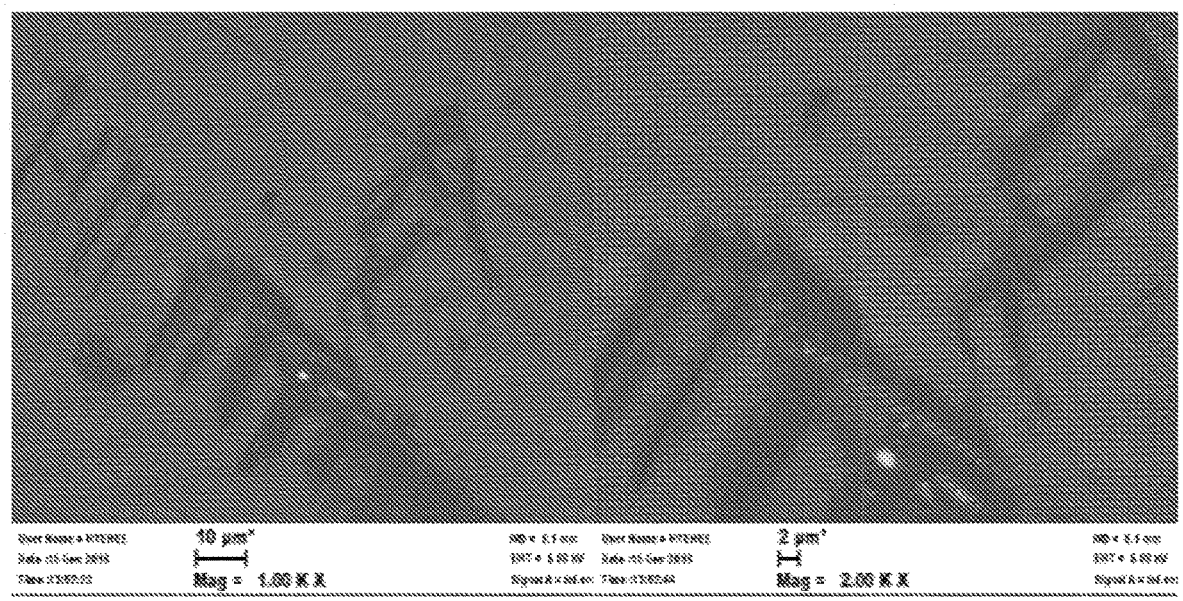
FIGS. 18A-18B present representative SEM and CV analysis data for biosensor electrodes made using photolithography, where the biosensor is produced using method comprising $H_2SO_4$ washing step and ferricyanide etching (or washing) step.
Figure 18A:
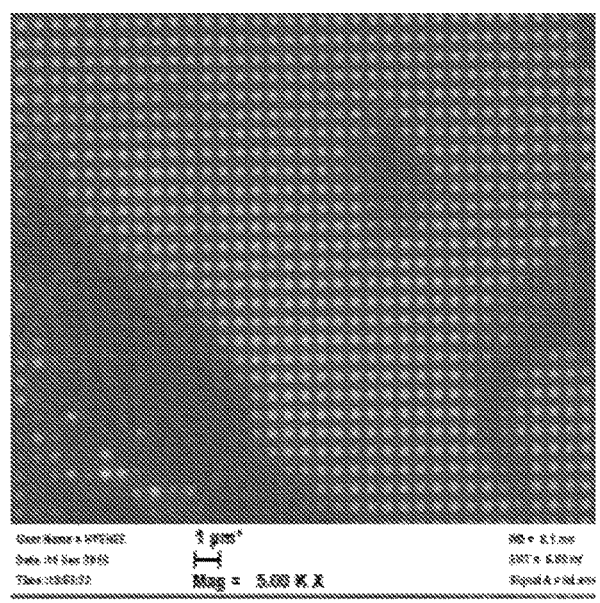
Figure 18B:
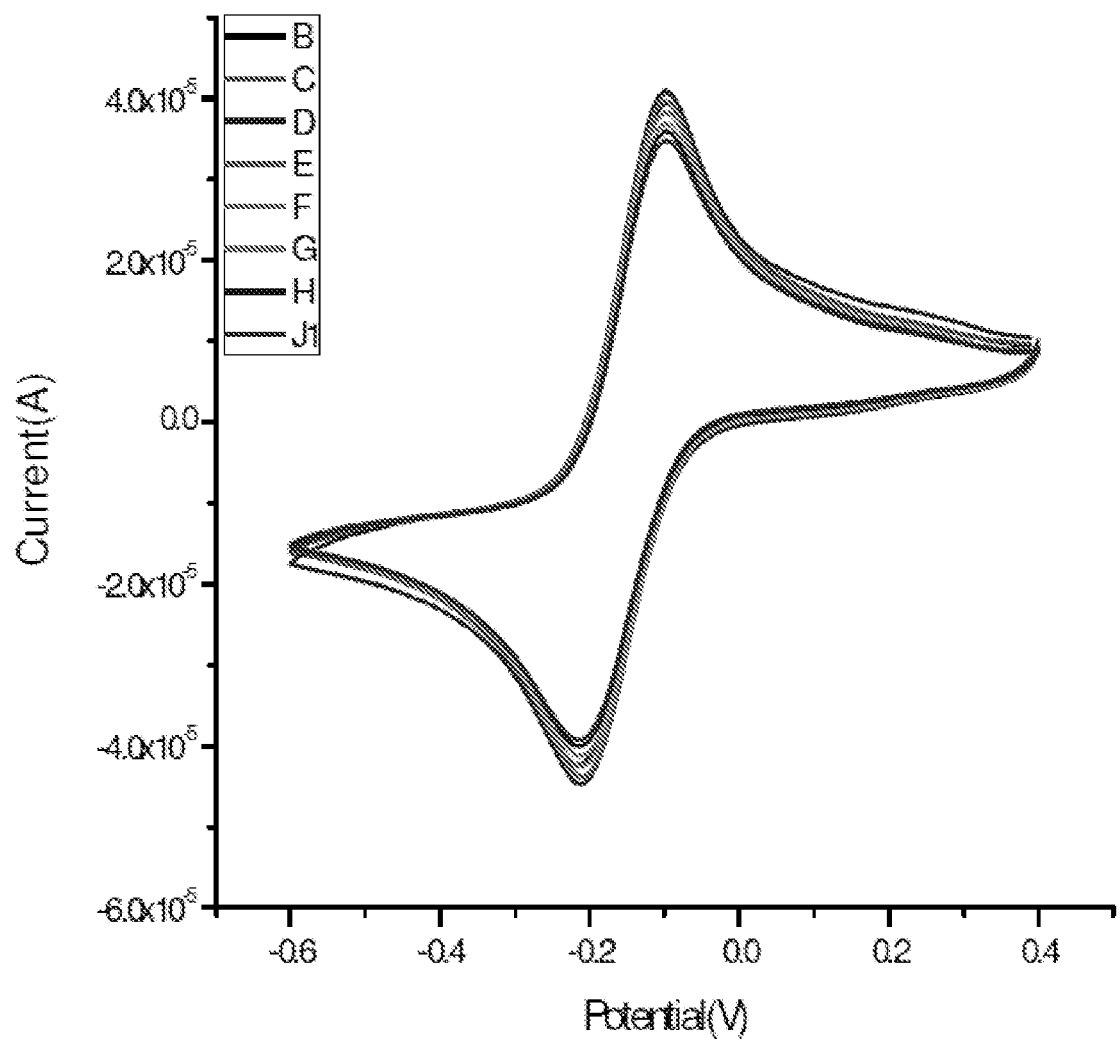

CV analysis data of FIGS. 16B, 17B, and 18B show poorly defined redox peak, which indicates higher levels of contamination of electrode surfaces with impurities as compared to nanowell array electrodes formed with $Si_3N_4$ or $SiO_2$ resist layers.

In some embodiments, the present disclosure may be adapted to be used with phosphate-buffered saline solution, for example, with respect to the ferricyanide etching step.

For example, CV analysis were measured in solutions containing 100 mM phosphate-buffered saline solution (pH 7.4) at a scan rate of 100 mV/s, with Init E as −0.6V and High E as +0.4V.

In some embodiments, the present disclosure may be adapted to be used using methylene blue (i.e., methylthioninium chloride) as washing solution, either in addition to the ferricyanide and/or $H_2SO_4$ washing, or without the ferricyanide and/or $H_2SO_4$ washing.

As shown in Example 1, a uniform and stable nanowell array surface is formed by using the insulation layer containing silicon nitride ($Si_3N_4$). The signals from the electrodes exposed to such nanowells can be precisely quantified, thereby greatly improving the sensitivity and selectivity of the biosensor.

Meanwhile, as shown in FIGS. 10B, 11B, and 12B, in Example 1A, redox peaks are rarely exhibited, while relatively well-defined redox peaks are exhibited in Example 1B. Especially, in Example 1C where the ferricyanide etching was included after the sulfuric acid washing, the most well-defined redox peaks are exhibited. Therefore, it appears that in the case of Example 1A, which did not include the washing process, significant impurities were present on the electrode surfaces, such that the electrode surfaces were not well exposed. By comparison, it is understood that in Examples 1B and 1C, which included the washing process, impurities on the bottom floors of the nanowells were removed and thus the electrode surfaces were normally exposed.

Example 2. Effects of Washing Electrodes Having $SiO_2$ Insulation Layer with $H_2SO_4$ and/or $K_3Fe(CN)_6$ In Example 2, biosensors were manufactured according to the same methods described in Example 1, except that the insulation layer for nanowells was formed with $SiO_2$, instead of $Si_3N_4$. In addition, the biosensors manufactured according to Example 2 underwent different washing processes as described in Table 3 below. Each washing process was carried out under the same conditions as described in Example 1.

TABLE 3

| Example | Sulfuric Acid ($H_2SO_4$) Washing | Ferricyanide Etching |
|---|---|---|
| Example 2A | X | X |
| Example 2B | O | X |
| Example 2C | O | O |

The nanowell array of the resultant biosensors, e.g., the biosensors manufactured by Examples 2A-2C, was photographed by SEM, and the CV analysis was carried out for each biosensor.

Figure 13B:
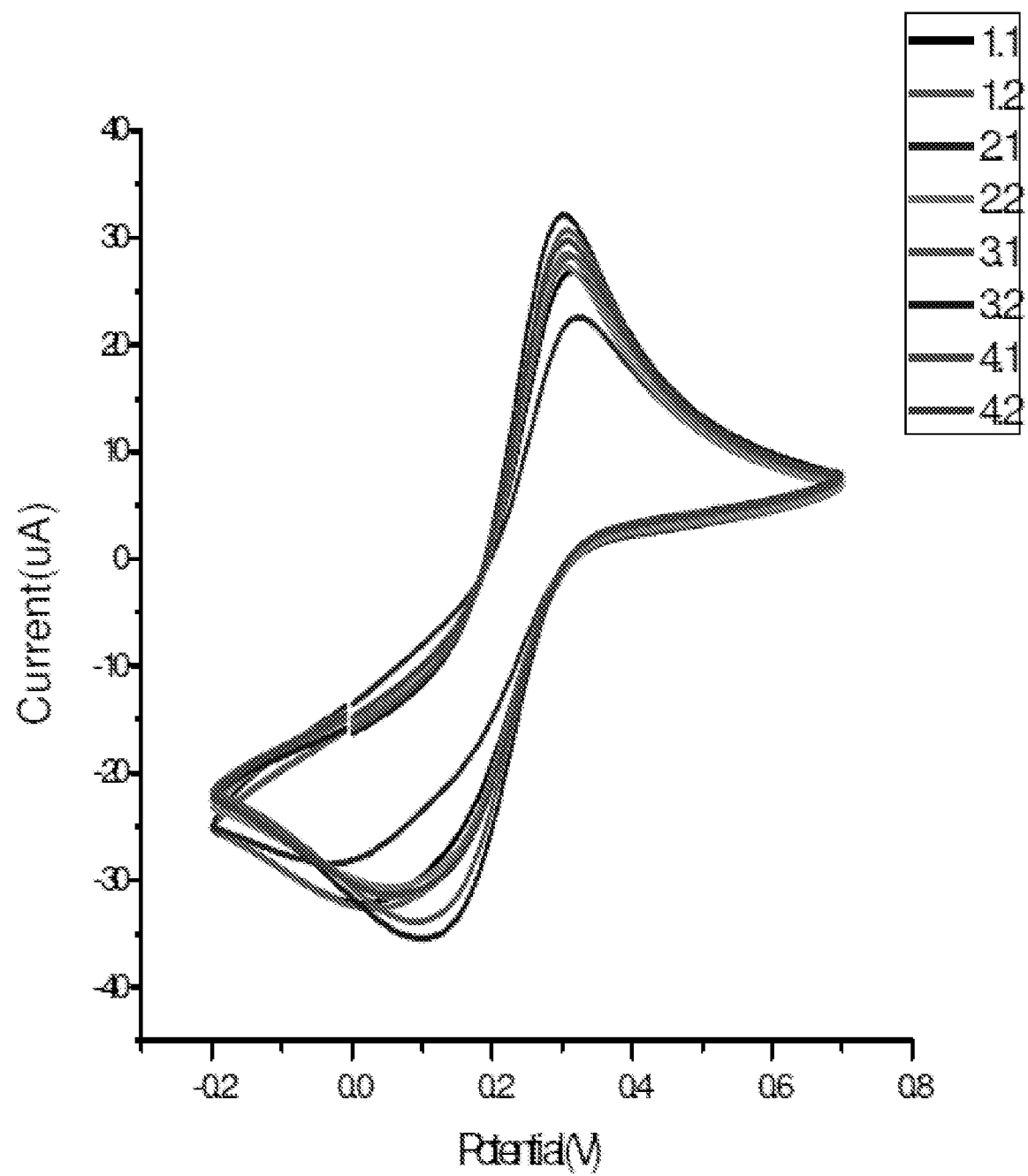
Figure 14A:
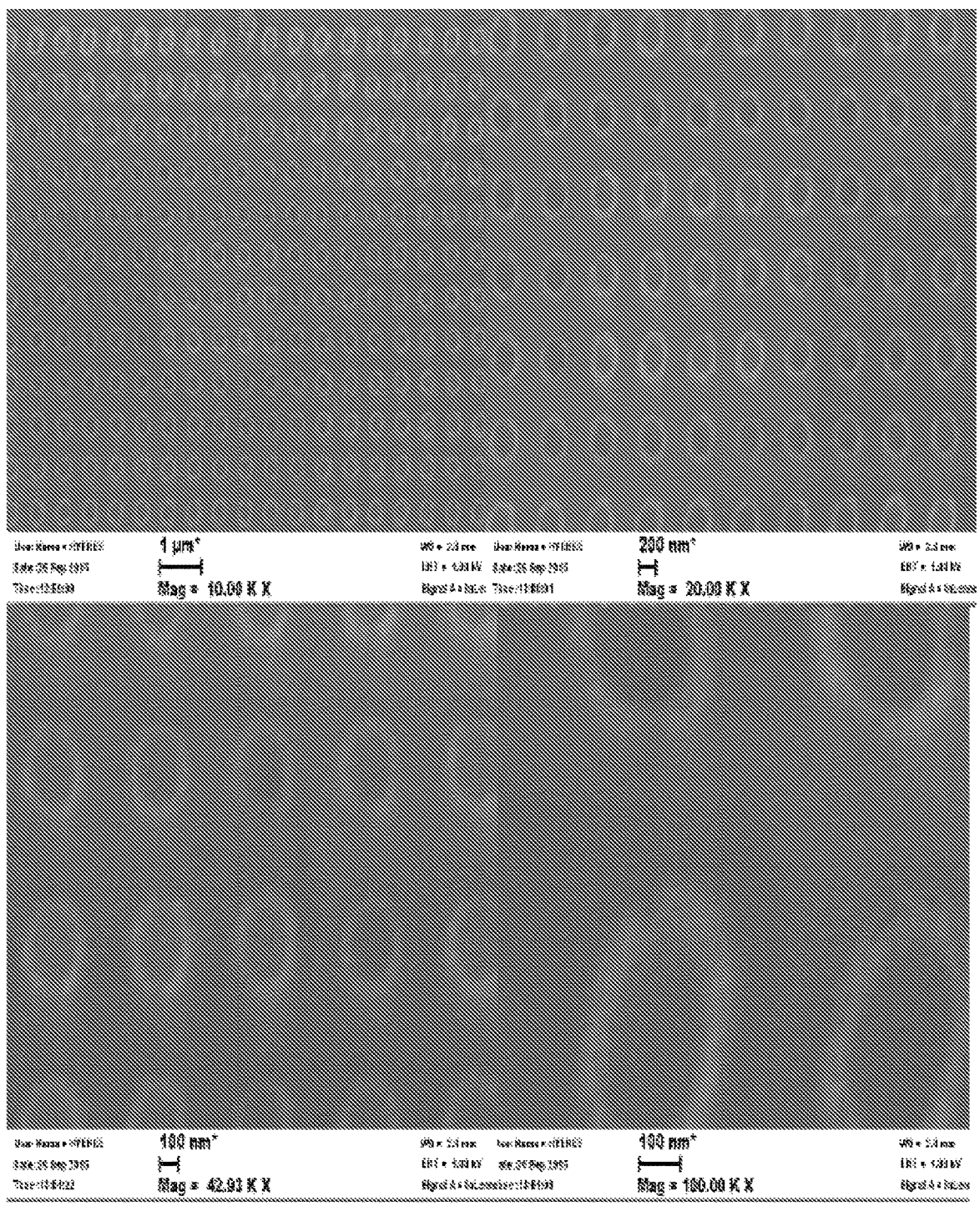
FIGS. 14A-14B present representative SEM and CV analysis data for biosensor electrodes comprising $SiO_2$ insulation layer, where the biosensor is produced using method comprising $H_2SO_4$ washing step.
Figure 14B:
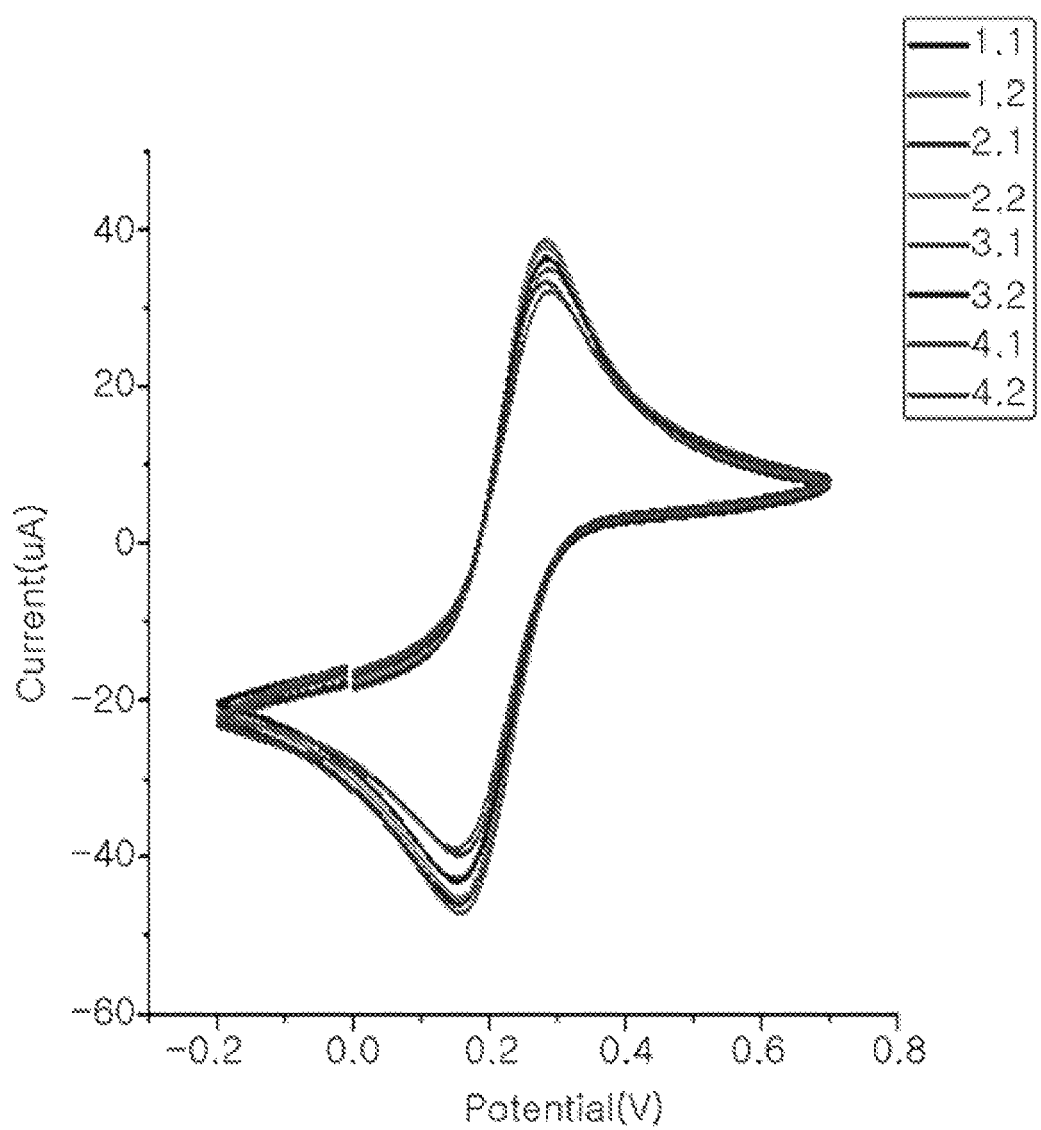
Figure 15A:
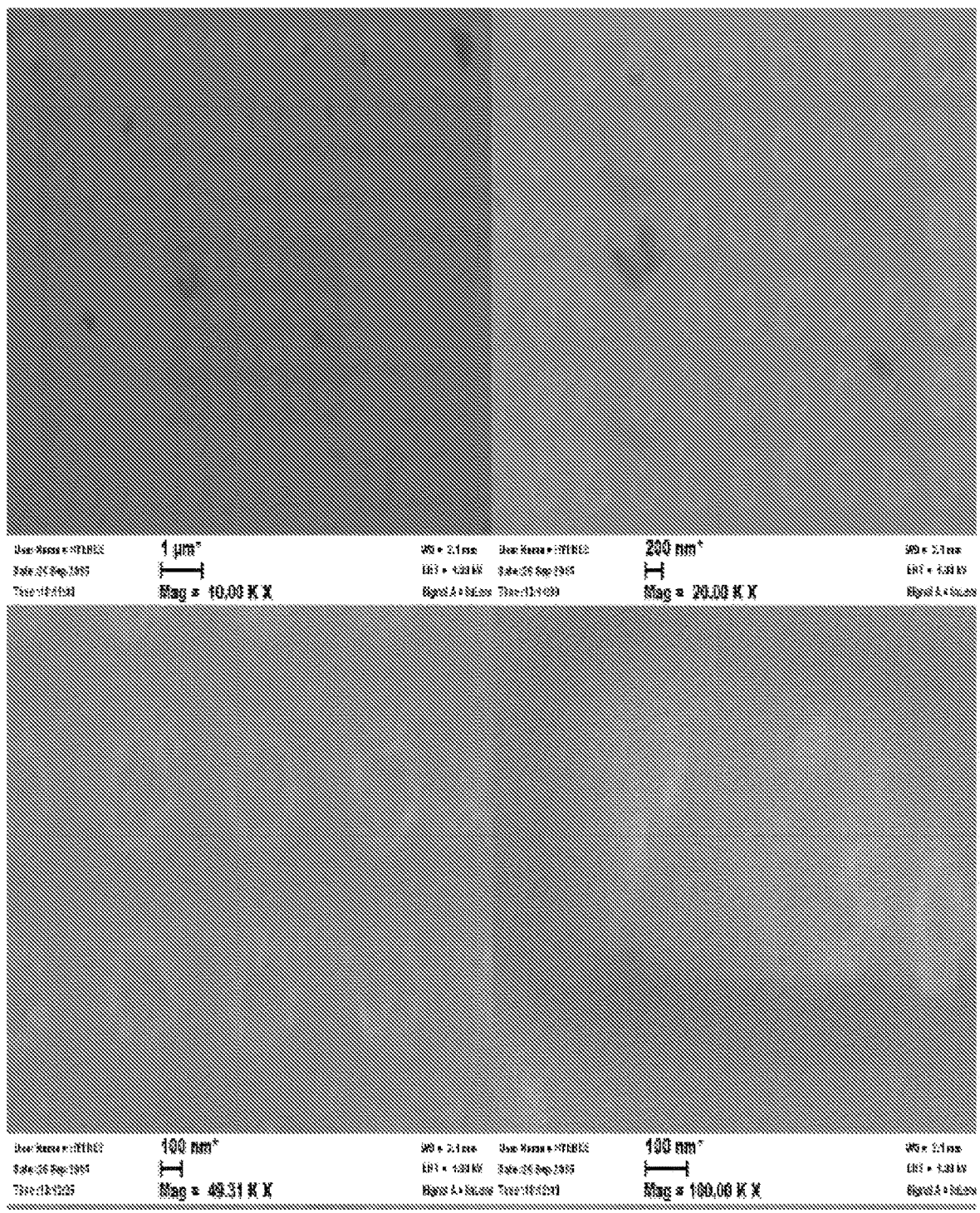
FIGS. 15A-15B present representative SEM and CV analysis data for biosensor electrodes comprising $SiO_2$ insulation layer, where the biosensor is produced using method comprising $H_2SO_4$ washing step and ferricyanide etching (or washing) step.
Figure 15B:
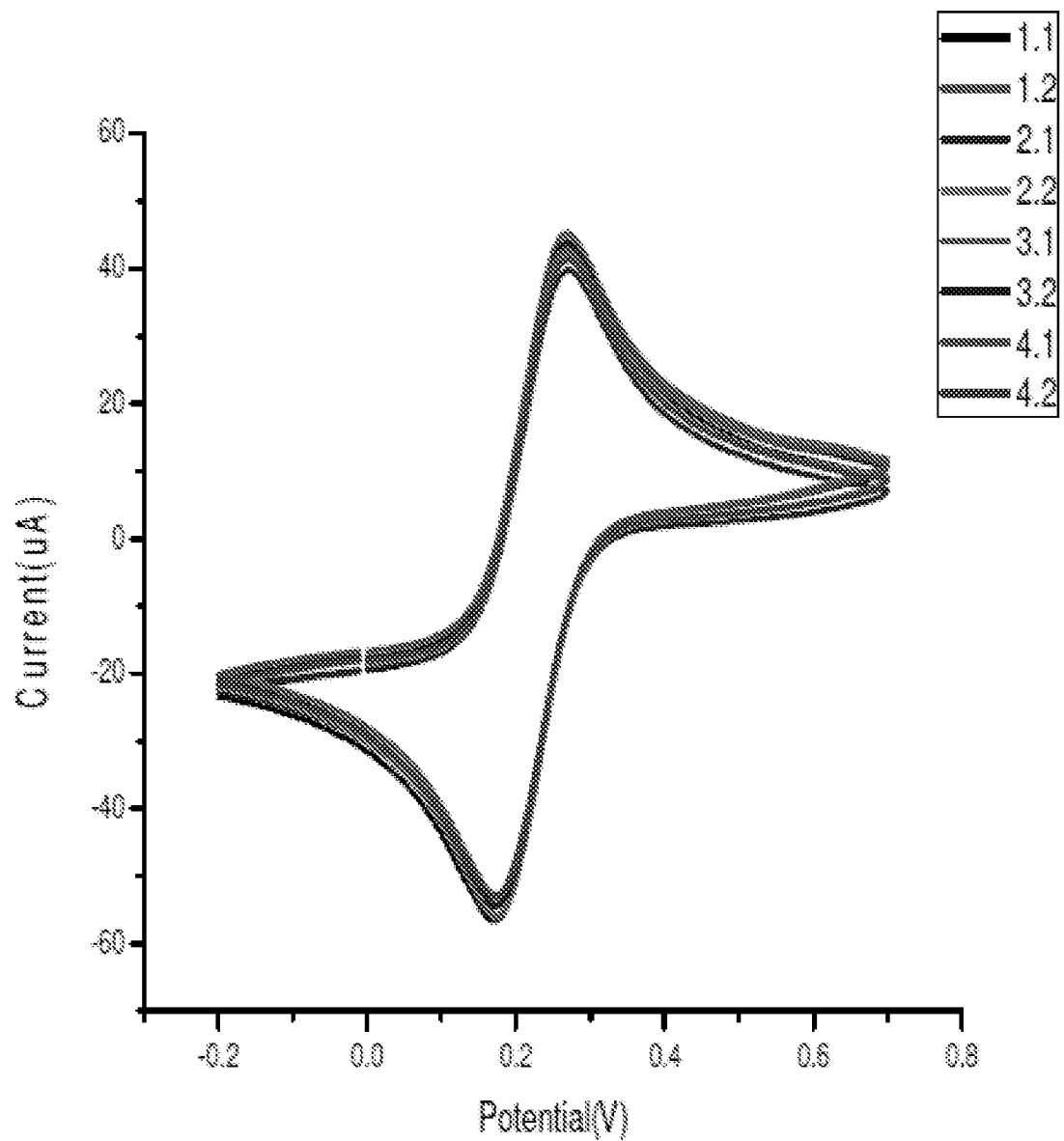

FIGS. 13A, 14A and 15A show SEM images of biosensors manufactured by employing different washing processes (Examples 2A-2C), and FIGS. 13B, 14B and 15B are graphs showing CV analysis data for biosensors of FIGS. 13A, 14A and 15A, respectively.

FIG. 13A shows SEM image of a nanowell array surface formed from $SiO_2$ resist layer. In this example, cleaning by $H_2SO_4$ or ferricyanide etching are not performed. Nanowells in uniform arrays are shown. As shown in the lower panel, each nanowell is approximately 230 nm in diameter and the nanowells are spaced with a pitch ratio of 1:1 (the scale bar in the SEM picture: 200 nm).

FIG. 13N shows CV analysis data for nanowell array electrodes exemplified in FIG. 13A.

FIG. 14A shows SEM image of a nanowell array surface formed from $SiO_2$ resist layer. In this example, $H_2SO_4$ washing step was performed. Nanowells in uniform arrays are shown. As shown in the lower panel, each nanowell is approximately 230 nm in diameter and the nanowells are spaced with a pitch ratio of 1:1 (the scale bar in the SEM picture: 200 nm).

FIG. 14B shows CV analysis data for nanowell array electrodes exemplified in FIG. 14A.

FIG. 15A shows SEM image of a nanowell array surface formed from $SiO_2$ resist layer. In this example, $H_2SO_4$ washing step and ferricyanide etching (or washing) step were performed. As shown in the lower panel, each nanowell is approximately 230 nm in diameter and the nanowells are spaced with a pitch ratio of 1:1 (the scale bar in the SEM picture: 200 nm).

FIG. 15B shows CV analysis data for nanowell array electrodes exemplified in FIG. 15A.

First, FIGS. 13A, 14A and 15A show that biosensors according to all Examples have nanowells in uniform arrays. Especially, as shown in the lower panel, each nanowell opening is approximately 230 nm in diameter and the nanowells are spaced with a pitch ratio of 1:1 (see SEM image with scale bar 200 nm).

As such, similar to the $Si_3N_4$ insulation layer as described in Example 1, a uniform and stable nanowell array surface can be formed by using $SiO_2$. The signals from the electrodes exposed to such nanowells can be precisely quantified, thereby greatly improving the sensitivity and selectivity of the biosensor.

As shown in FIGS. 13B, 14B, and 15B, relatively normal oxidation current peaks are exhibited, but reduction current peaks are not exhibited in Example 2A. By comparison, in Example 2B, which included the sulfuric acid washing, relatively well-defined reduction current peaks are also exhibited. Especially, in Example 2C where the ferricyanide etching was included after the sulfuric acid washing, the most well-defined redox peaks are exhibited. Therefore, it is understood that through the washing process, impurities on the bottom floors of the nanowells were removed and thus the electrode surfaces were normally exposed.

Comparative Example. Effects of Washing Electrodes Having Insulation Layer Formed by Photolithography with $H_2SO_4$ and/or $K_3Fe(CN)_6$ In Comparative Example, biosensors were manufactured according to the same methods described in Examples 1 and 2, except that the insulation layer for nanowells was formed by using a photoresist material, instead of inorganic insulator layers such as $SiO_2$ or $Si_3N_4$. In addition, the biosensors manufactured according to Comparative Example underwent different washing processes as described in Table 4 below. Each washing process was carried out under the same conditions as described in Examples 1 and 2.

TABLE 4

| Example | Sulfuric Acid (H$_2$SO$_4$) Washing | Ferricyanide Etching |
|---|---|---|
| Comparative Example A | X | X |
| Comparative Example B | O | X |
| Comparative Example C | O | O |

The nanowell array of the resultant biosensors, e.g. the biosensors manufactured by Comparative Examples A-C, was photographed by SEM, and the CV analysis was carried out for each biosensor.

FIGS. 16A, 17A and 18A show SEM images of biosensors manufactured by employing different washing processes (Comparative Examples A-C), and FIGS. 16B, 17B and 18B are graphs showing CV analysis data for biosensors of FIGS. 16A, 17A and 18A, respectively.

Effects of Washing Electrodes Having Insulation Layer Formed by Photolithography with H$_2$SO$_4$ and/or K$_3$Fe(CN)$_6$, as shown in FIGS. 14A-16B.

FIG. 16A shows SEM image of a nanowell array surface formed using photolithography. In this example, cleaning by H$_2$SO$_4$ or ferricyanide etching is not performed. Nanowells in uniform arrays are shown. As shown in the lower panel, each nanowell is approximately 230 nm in diameter and the nanowells are spaced with a pitch ratio of 1:1 (the scale bar in the SEM picture: 200 nm).

FIG. 16B shows CV analysis data for nanowell array electrodes exemplified in FIG. 16A.

FIG. 17A shows SEM image of a nanowell array surface formed using photolithography. In this example, H$_2$SO$_4$ washing step was performed. Nanowells in uniform arrays are shown. As shown in the lower panel, each nanowell is approximately 230 nm in diameter and the nanowells are spaced with a pitch ratio of 1:1 (the scale bar in the SEM picture: 200 nm).

FIG. 17B shows CV analysis data for nanowell array electrodes exemplified in FIG. 17A.

FIG. 18A shows SEM image of a nanowell array surface formed using photolithography. In this example, H$_2$SO$_4$ washing step and ferricyanide etching (or washing) step were performed. Nanowells in uniform arrays are shown. As shown in the lower panel, each nanowell is approximately 230 nm in diameter and the nanowells are spaced with a pitch ratio of 1:1 (the scale bar in the SEM picture: 200 nm).

FIG. 18B shows CV analysis data for nanowell array electrodes exemplified in FIG. 18A.

First, FIGS. 16A, 17A and 18A show that biosensors according to Comparative Example 1 have nanowells in uniform arrays, each nanowell opening is approximately 230 nm in diameter, and the nanowells are spaced with a pitch ratio of 1:1, similar to other Examples. However, in Examples B and C, which included washing processes, the nanowells of the photoresist insulating layer are collapsed or damaged. As such, the organic insulator layer, such as photoresist, is not suitable for introducing the washing process of the present invention, because it causes a chemical reaction with the solution applied to the washing process.

In FIGS. 16B, 17B, and 18B, well-defined redox peaks are not exhibited, which indicate that the electrode surfaces were not well exposed due to significant impurities.

In certain embodiments, the methods of production disclosed herein results in electrodes of the biosensors having improved electrochemical properties. In one preferred embodiment, the electrochemical properties are measured using cyclic voltammetry analysis.

In certain embodiments, the scan cycle of the Fe(CN)$_6$ washing step comprises one cycle or two cycles. In certain other embodiments, the scan cycle of the Fe(CN)$_6$ washing step comprises more than two cycles.

It is well known in the art that generally, Fe(CN)$_6$ washing conditions comprising application of electric current with a voltage of greater than 1 V is likely to adversely affect the surface integrity of the electrodes. However, in certain embodiments of the present disclosure, electric current with a voltage of greater than 1 V is applied for a short duration to yield unexpectedly advantageous results, such as removal of impurities and enhanced electrochemical properties of electrodes of biosensors. In certain other embodiments, similar unexpectedly advantageous results can occur with Fe(CN)$_6$ washing conditions comprising application of electric current with a voltage of 0.9-1.5 V, 1.0-1.4 V, 1.1-1.3 V, or 1.15-1.25 V.

As described previously, insulation layers providing nanowells can consist with materials, which do not react during the washing Fe(CN)6 washing step, such as inorganic materials. In some embodiments, insulation layers can be formed using inorganic materials, instead of organic materials, such as photoresist material. Especially, some embodiments of the present disclosure are especially well suited for electrochemical biosensors that comprise insulation layers made of Si3N4 or SiO2. In some embodiments, the present disclosure is not well suited for photolithography of electrochemical biosensors comprising insulation layers having nanowells due to Weak bonding between electrodes (e.g., gold) and the insulation layers.

In some embodiments, the present disclosure may be adapted to be used with phosphate-buffered saline solution in addition to the solutions described, for example, with respect to the ferricyanide etching step.

EXEMPLARY EMBODIMENTS OF BIOSENSORS AND USE THEREOF

An electrochemical biosensor device for sensing presence of a molecule in solution, the device comprising:
a substrate layer; and
a plurality of electrodes, the electrodes further comprising:
  a buffer layer laid on the substrate layer, the buffer layer configured to provide bonding of the plurality of electrodes to the substrate layer;
  an electrode layer laid on the buffer layer, the electrode layer configured to provide binding sites for analytes; and
  an insulator layer having a plurality of bores, the insulator layer laid on the electrode layer and the insulator having a plurality of bores configured to form a plurality of nanowells having side walls that are defined by the insulator layer and having bottom floors that are defined by a top surface of the electrode layer that is not covered by the insulator layer,
  wherein an analyte probe is immobilized to the bottom floors of the nanowells, the analyte probe configured to bind to an analyte, and
  wherein the insulator layer is configured to substantially confine binding of the analyte to the top surface of the electrode layer that define the bottom floors of the plurality of nanowells.

The electrochemical biosensor device according to claim 1, wherein the substrate layer comprises glass.

The electrochemical biosensor device according to claim 1, wherein the substrate layer comprises silicon.

The electrochemical biosensor device according to claim 1, wherein the insulator layer comprises silicon nitride.

The electrochemical biosensor device according to claim 1, wherein the insulator layer comprises silicon dioxide.

The electrochemical biosensor device according to claim 1, wherein the buffer layer comprises titanium.

The electrochemical biosensor device according to claim 1, wherein the buffer layer comprises chromium.

The electrochemical biosensor device according to claim 1, wherein the electrode layer comprises gold.

The electrochemical biosensor device according to claim 1, wherein the nanowell is cylindrical in shape and has a circular nanowell opening with a diameter of about 230 nm.

The electrochemical biosensor device according to claim 1, wherein the nanowell is cylindrical in shape and has a circular nanowell opening with a diameter of about 100 nm.

The electrochemical biosensor device according to claim 1, wherein the nanowell is cylindrical in shape and has a nanowell opening with a diameter of about 50 am.

The electrochemical biosensor device according to claim 1, wherein the pitch ratio between the plurality of nanowells is less than 1:5.

The electrochemical biosensor device according to claim 1, wherein the pitch ratio between the plurality of nanowells is less than 1:3.

The electrochemical biosensor device according to claim 1, wherein the pitch ratio between the plurality of nanowells is about 1:1.

The electrochemical biosensor device according to claim 1, wherein the device is capable of sending signals to an electronic device, such that differences in one or more electrochemical reaction parameters between the electrode containing a reference sample and the electrode containing a test sample can be detected by the electronic device using the signals to determine whether the analyte is present in the test sample.

The electrochemical biosensor device according to claim 9, wherein the electrochemical reaction comprises oxidation reaction and reduction reaction.

The electrochemical biosensor device according to claim 9, wherein the parameters comprise variation in redox current.

Method of detecting an analyte in a test sample using the biosensor device according to claim 1, the method comprising steps of:
applying the test sample to the sensing electrode of the electrochemical biosensor device in such a manner that an analyte that may be present in the test sample is able to bind to the analyte probe;
rinsing the sensing electrodes with an appropriate buffer in such a manner that washes away non-bound and/or non-specifically bound analytes and non-analytes to be removed from the sensing electrode;
applying electric current to the sensing electrode in such a way to cause chemical changes to the sensing electrode;
measuring electrochemical properties of the sensing electrode using an electronic device; and
analyzing differences in electrochemical properties between the test sample and the reference sample to determine presence of an analyte on the sensing electrode.

The method according to claim 12 wherein, electrochemical properties of the sensing electrode is measured using cyclic voltammetry.

While the foregoing description has been directed to specific embodiments, it will be apparent that other variations and modifications may be made to the described embodiments, with the attainment of some or all of their advantages. Accordingly, this description is to be taken only by way of example and not to otherwise limit the scope of the embodiments herein. Therefore, it is the object of the appended claims to cover all such variations and modifications as come within the true spirit and scope of the embodiments described herein. Finally, all publications and references cited herein are expressly incorporated by reference in their entirety.

A person skilled in the art will appreciate that, although the present disclosure is called "biosensors," its application is not limited to detection of biological molecules. In other words, the present disclosure may be used for detection of other small non-biological (e.g., inorganic, metallic, solute, electrolyte, and/or elemental) molecules. In addition, although examples provided here consist of detection in fluidic and/or aqueous milieu, one skilled in the art will appreciate that the present disclosure may be used to detect small molecules in other fluidic milieu such as in oil, solvents, gas, and/or colloidal solutions.

The invention claimed is:

1. A method of manufacturing a biosensor, the method comprising:
    forming a buffer layer on a substrate layer;
    forming a metal layer on the buffer layer;
    forming a desired patterned electrode by patterning the metal layer using a first photolithography process;
    forming an inorganic insulation layer on the desired patterned electrode;
    forming a plurality of a nanowell on the inorganic insulation layer by exposing an area of the desired patterned electrode using a second photolithography process;
    washing the plurality of the nanowell with a sulfuric acid ($H_2SO_4$) solution to remove an impurity from the desired patterned electrode exposed by the plurality of the nanowells; and
    washing the plurality of the nanowell by a ferricyanide etching after washing with the sulfuric acid ($H_2SO_4$) solution,
    wherein the ferricyanide etching is performed by immersing the biosensor in a mixed solution of $K_3Fe(CN)_6$ and KCl, and applying a voltage of 0.9-1.5 V.

2. The method of claim 1, wherein the ferricyanide etching is performed at a temperature in a range of 15-25° C. for 1 to 10 seconds.

3. The method of claim 1, wherein the desired patterned electrode comprises gold (Au).

4. The method of claim 1, wherein the inorganic insulation layer comprises $SiO_2$ or $Si_3N_4$.

5. The method of claim 1, wherein the step of washing the plurality of the nanowell with the sulfuric acid ($H_2SO_4$) solution is by immersing the biosensor in the sulfuric acid ($H_2SO_4$) solution and applying a voltage of 1.0-1.5 V for 1-5 minutes.

6. The method of claim 1, wherein a pitch ratio of the plurality of the nanowell is defined as a size of each nanowell to the shortest distance between adjacent nanowell, wherein the pitch ratio is 1:3 or less.

7. A method of manufacturing a biosensor, the method comprising:
   forming an electrode on a substrate layer;
   forming an inorganic insulation layer on the electrode;
   forming a plurality of a nanowell on the inorganic insulation layer by exposing an area of the electrode using a photolithography process;
   first washing by immersing the plurality of the nanowell into a $H_2SO_4$ solution and applying a voltage of 1.5-2.0 V; and
   second washing by immersing the plurality of the nanowells into a mixed solution of $K_3Fe(CN)_6$ and KCl and applying a voltage of 1.0-1.5 V.

* * * * *